(12) United States Patent
Belichard

(10) Patent No.: US 9,107,928 B2
(45) Date of Patent: *Aug. 18, 2015

(54) COMPOSITIONS AND METHODS FOR TREATING OPHTHALMIC DISORDERS

(75) Inventor: Pierre Belichard, Paris (FR)

(73) Assignee: Dyax Corp., Burlington, MA (US)

( * ) Notice: Subject to any disclaimer, the term of this patent is extended or adjusted under 35 U.S.C. 154(b) by 644 days.

This patent is subject to a terminal disclaimer.

(21) Appl. No.: 12/792,393

(22) Filed: Jun. 2, 2010

(65) Prior Publication Data

US 2010/0273721 A1 Oct. 28, 2010

Related U.S. Application Data

(63) Continuation of application No. 11/724,197, filed on Mar. 15, 2007.

(30) Foreign Application Priority Data

Mar. 16, 2006 (EP) ..................................... 06360008
Sep. 26, 2006 (EP) ..................................... 06291516

(51) Int. Cl.
| | | |
|---|---|---|
| A61K 38/00 | (2006.01) | |
| A61P 27/02 | (2006.01) | |
| C07K 2/00 | (2006.01) | |
| A61K 38/57 | (2006.01) | |

(52) U.S. Cl.
CPC ..................................... *A61K 38/57* (2013.01)

(58) Field of Classification Search
CPC ........... A61K 38/00; A61K 38/57; C07K 2/00
See application file for complete search history.

(56) References Cited

U.S. PATENT DOCUMENTS

| | | | |
|---|---|---|---|
| 5,217,951 | A | 6/1993 | Lezdey et al. |
| 5,795,865 | A | 8/1998 | Markland et al. |
| 5,994,125 | A | 11/1999 | Markland et al. |
| 6,010,880 | A | 1/2000 | Markland et al. |
| 6,057,287 | A | 5/2000 | Markland et al. |
| 6,174,859 | B1 | 1/2001 | Lezdey et al. |
| 6,333,402 | B1 | 12/2001 | Markland et al. |
| 6,989,369 | B2 | 1/2006 | Ladner et al. |
| 7,064,107 | B2 | 6/2006 | Ladner et al. |
| 7,153,829 | B2 | 12/2006 | Ladner et al. |
| 7,166,576 | B2 | 1/2007 | Cicardi et al. |
| 7,235,530 | B2 | 6/2007 | Blair et al. |
| 7,276,480 | B1 | 10/2007 | Ladner et al. |
| 7,550,427 | B2 | 6/2009 | Ley et al. |
| 7,628,983 | B2 | 12/2009 | Markland et al. |
| 7,704,949 | B2 | 4/2010 | Ladner et al. |
| 7,718,617 | B2 | 5/2010 | Cicardi et al. |
| 2004/0027782 | A1 | 2/2004 | Ladner et al. |
| 2004/0038893 | A1 | 2/2004 | Ladner et al. |
| 2004/0053206 | A1 | 3/2004 | Cicardi et al. |
| 2004/0171794 | A1 | 9/2004 | Ladner et al. |
| 2005/0089515 | A1 | 4/2005 | Ley et al. |
| 2005/0164928 | A1 | 7/2005 | Ladner et al. |
| 2005/0222023 | A1 | 10/2005 | Hauser et al. |
| 2006/0069020 | A1 | 3/2006 | Blair et al. |
| 2006/0194727 | A1 | 8/2006 | Ladner et al. |
| 2007/0020252 | A1 | 1/2007 | Ladner et al. |
| 2007/0049522 | A1 | 3/2007 | Ladner et al. |
| 2007/0213275 | A1 | 9/2007 | Clark et al. |
| 2007/0249807 | A1 | 10/2007 | Ladner et al. |
| 2007/0270344 | A1 | 11/2007 | Belichard |
| 2008/0064637 | A1 | 3/2008 | Ladner et al. |
| 2008/0076712 | A1 | 3/2008 | Ladner et al. |
| 2008/0131426 | A1 | 6/2008 | Ladner et al. |
| 2008/0139473 | A1 | 6/2008 | Ladner et al. |
| 2008/0152656 | A1 | 6/2008 | Ladner et al. |
| 2008/0188409 | A1 | 8/2008 | Blair et al. |
| 2008/0200646 | A1 | 8/2008 | Ladner et al. |
| 2008/0221031 | A1 | 9/2008 | Blair et al. |
| 2008/0226655 | A1 | 9/2008 | Ladner et al. |
| 2008/0260752 | A1 | 10/2008 | Ladner et al. |
| 2008/0274969 | A1 | 11/2008 | Hauser et al. |

(Continued)

FOREIGN PATENT DOCUMENTS

| | | |
|---|---|---|
| WO | WO 95/21601 A2 | 8/1995 |
| WO | WO 03/066824 A2 | 8/2003 |

(Continued)

OTHER PUBLICATIONS

Hypertensive Retinopathy-Merck manual, pp. 1-2, accessed Sep. 26, 2013.*
Central and Branch Retinal Artery Occlusion-Merck Manual, pp. 1-3, accessed Sep. 26, 2013.*
Diabetic Retinopathy-Merck Manual. pp. 1-3, accessed Sep. 26, 2013.*
Retinopathy of Prematurity-Merck Manual, pp. 1-2, accessed Sep. 26, 2013.*
Retinal Vascular Diseases, from http://dro.hs.columbia.edu/vr3.htm, enclosed pp. 1-2, accessed Sep. 26, 2013.*
Barnard, Retinal Vascular Disorders, from http://www.academy.org.uk/lectures/barnard5.htm, pp. 1-4, accessed Sep. 26, 2013.*
Sonoda et al., [Ophthalmological (retinal) pathology and inflammation.] Kekkann Igaku. Oct. 2003;4(5):61-66.
Devani et al., Kallikrein-kinin system in inflammatory bowel diseases: Intestinal involvement and correlation with the degree of tissue inflammation. Dig Liver Dis. Sep. 2005;37(9):665-73.
U.S. Appl. No. 08/179,964, filed Jan. 11, 1994.
U.S. Appl. No. 10/016,329, Markland, filed Oct. 26, 2001.

(Continued)

*Primary Examiner* — Julie Ha
*Assistant Examiner* — Li Ni Komatsu
(74) *Attorney, Agent, or Firm* — Wolf, Greenfield & Sacks, P.C.

(57) ABSTRACT

The present invention relates to compositions and methods for treating ophthalmic disorders of humans or animals. The present compositions and methods are highly suitable for intraocular administration into the interior of an eye and provide therapeutic effects to the eye as they are effective in stabilizing, enhancing and/or improving a patient's vision. More specifically, the present invention relates to compositions and methods for treating ophthalmic diseases or disorders with exudative, hemorrhagic and/or inflammatory conditions. Even more specifically, the present invention relates to compositions and methods for treating retinal diseases or disorders, and more specifically ophthalmic diseases or disorders related to impaired retinal vessel permeability and/or integrity.

3 Claims, 2 Drawing Sheets

(56) References Cited

U.S. PATENT DOCUMENTS

Figure 1:
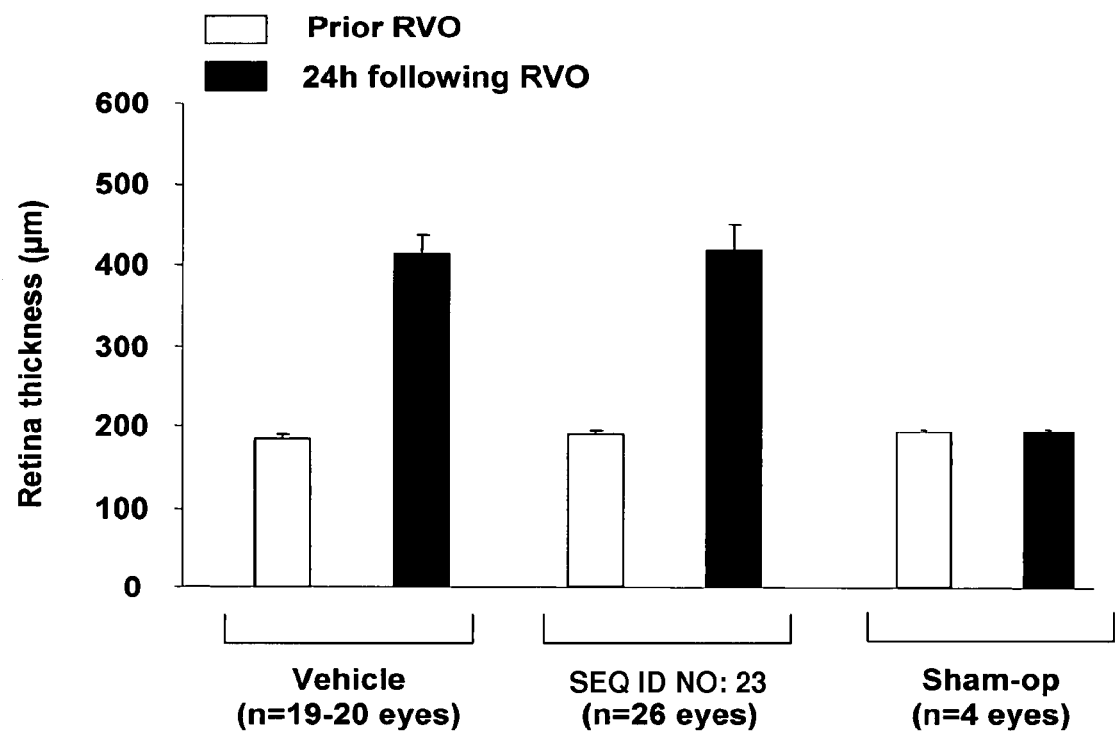

| | | | |
|---|---|---|---|
| 2008/0280811 | A1 | 11/2008 | Feener et al. |
| 2009/0062195 | A1 | 3/2009 | Ladner et al. |
| 2009/0075887 | A1 | 3/2009 | McPherson |
| 2009/0082267 | A1 | 3/2009 | Ladner et al. |
| 2009/0105142 | A1 | 4/2009 | Moscicki |
| 2009/0117130 | A1 | 5/2009 | Ladner et al. |
| 2009/0221480 | A1 | 9/2009 | Blair et al. |
| 2009/0227494 | A1 | 9/2009 | Blair et al. |
| 2009/0227495 | A1 | 9/2009 | Blair et al. |
| 2009/0233852 | A1 | 9/2009 | Blair et al. |
| 2009/0234009 | A1 | 9/2009 | Blair et al. |
| 2009/0247453 | A1 | 10/2009 | Blair et al. |
| 2009/0264350 | A1 | 10/2009 | Blair et al. |
| 2010/0034805 | A1 | 2/2010 | Ladner et al. |
| 2010/0273721 | A1 | 10/2010 | Belichard |

FOREIGN PATENT DOCUMENTS

| | | | |
|---|---|---|---|
| WO | WO 03/103475 | A2 | 12/2003 |
| WO | WO 2004/019968 | A1 | 3/2004 |
| WO | WO 2005/021556 | A2 | 3/2005 |
| WO | WO 2005/021557 | A2 | 3/2005 |
| WO | WO 2006/036860 | A2 | 4/2006 |
| WO | WO 2006/091459 | A2 | 8/2006 |
| WO | WO 2007/104541 | A2 | 9/2007 |
| WO | WO 2007/106746 | A2 | 9/2007 |
| WO | WO 2009/026334 | A2 | 2/2009 |
| WO | WO 2009/026539 | A1 | 2/2009 |
| WO | WO 2010/048432 | A1 | 4/2010 |

OTHER PUBLICATIONS

U.S. Appl. No. 12/580,903, Markland et al., filed Jan. 6, 2010.
U.S. Appl. No. 12/683,094, Sternlicht et al., filed Aug. 24, 2010.
U.S. Appl. No. 60/335,547, filed Feb. 7, 2002.
U.S. Appl. No. 60/387,239, Ladner, filed Jun. 7, 2002.
U.S. Appl. No. 60/407,003, Ladner, filed Aug. 28, 2002.
U.S. Appl. No. 60/407,004, Cicardi, filed Aug. 28, 2002.
U.S. Appl. No. 60/498,845, Ladner, filed Aug. 29, 2003.
U.S. Appl. No. 60/598,967, Ladner, filed Aug. 4, 2004.
U.S. Appl. No. 60/781,444, Clark, filed Mar. 10, 2006.
U.S. Appl. No. 60/956,952, McPherson, filed Aug. 21, 2007.
U.S. Appl. No. 60/957,526, Moscicki, filed Aug. 23, 2007.
U.S. Appl. No. 61/107,384, Wood, filed Oct. 22, 2008.
U.S. Appl. No. 61/142,746, Sternlicht, filed Jan. 6, 2009.
U.S. Appl. No. 10/930,344, Ladner, filed Aug. 30, 2004.
U.S. Appl. No. 11/141,770, Ladner, filed Jun. 1, 2005.
U.S. Appl. No. 11/860,853, Ladner et al., filed Sep. 25, 2007.
U.S. Appl. No. 11/930,700, Ladner et al., filed Oct. 31, 2007.
U.S. Appl. No. 12/471,875, Ley et al., filed May 26, 2009.
Ciulla et al., Diabetic retinopathy and diabetic macular edema: pathophysiology, screening, and novel therapies. Diabetes Care. Sep. 2003;26(9):2653-64.
Dennis et al., Potent and selective Kunitz domain inhibitors of plasma kallikrein designed by phage display, J Biol Chem. Oct. 27, 1995;20(43):25411-7.
Dotsenko et al., "Hageman factor and kallikrein in pathogenesis of senile cataracts and the pseudoexfoliation syndrome." Immunopharmacology. 1996; 32(1-3):141-5. Biosis Abstract. Accession No. PREV199699088025.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gao et al., Kallikrein-binding protein inhibits retinal neovascularization and decreases vascular leakage. Diabetologia. May 2003;46(5):689-98. Epub May 13, 2003.
Han Lee et al., Approaches toward reversal of increased vascular permeability in C1 inhibitor deficient mice. Immunol Lett. Oct. 31, 2003;89(2-3):155-60.
Hatcher et al, Kallikrein-binding protein levels are reduced in the retinas of streptozotocin-induced diabetic rats. Invest Ophthalmol Vis Sci. Mar. 1997;38(3):658-64.
Ley et al., Obtaining a family of high-affinity, high-specificity protein inhibitors of plasmin and plasma kallikrein. Mol Divers. Oct. 1996;2(1-2):119-24.
Ma et al., "Expression and cellular localization of the kallikrein-kinin system in ocular tissues." Experimental Eye Res. 1996; 63: 19-26.
Ma et al., "Kallistatin in human ocular tissues: reduced levels in vitreous fluids from patients with diabetic retinopathy." Current Eye Res. Nov. 1996;15(11):1117-23. Medline Abstract. Accession No. NLM8950506.
Ma et al., "Treatment of retinal edema using peptide angiogenic inhibitors." Ann Meeting of the Assoc for Res in Vision and Opthalmology. Fort Lauderdale, FL. May 4-8, 2003. Abstract 4029. Biosis accession No. PREV200300538899.
Markland et al., Iterative optimization of high-affinity protease inhibitors using phage display. 2. Plasma kallikrein and thrombin. Biochemistry. Jun. 18, 1996;35(24):8058-67.
Tanaka et al., Evaluation of a novel kallikrein inhibitor on hemostatic activation in vitro. Thromb Res. 2004;113(5):333-9.
Veloso et al., A monoclonal anti-human plasma prekallikrein antibody that inhibits activation of prekallikrein by factor XIIa on a surface. Blood. Oct. 1987;70(4):1053-62.
Williams et al., DX-88 and HAE: a developmental perspective. Transfus Apher Sci. Dec. 2003;29(3):255-8.
Delaria, et al., "Characterization of Placental Bikunin, a Novel Human Serine Protease Inhibitor," J. Biol. Chem., 1997, 272, pp. 12209-12214.
Examination Report for Canadian Application No. 2,646,285 dated Oct. 2, 2013.
Extended European Search Report received for EP 07005182.6 dated May 15, 2008.
Final Office Action received for U.S. Appl.No. 11/724,197 dated Jun. 2, 2011.
Final Office Action received for U.S. Appl. No. 11/724,197 dated Feb. 21, 2014.
International Search Report and Written Opinion received for PCT/EP2007/002216 dated May 15, 2008.
Marlor, et al., "Identification and Cloning of Human Placental Bikunin, A Novel Serine Protease Inhibitor Containing Two Kunitz Domains," J. Bil. Chem., 1997, 272, 12202-12208.
Non-final Office Action on U.S. Appl. No. 11/724,197 dated Dec. 18, 2009.
US Office Action on U.S. Application No. 11/724,197 dated Aug. 19, 2013.
US Office Action for Application U.S. Appl. No. 11/724,197 dated Sep. 8, 2014 (13 pages).

\* cited by examiner

COMPOSITIONS AND METHODS FOR TREATING OPHTHALMIC DISORDERS

RELATED APPLICATIONS

The present application is a continuation of U.S. application Ser. No. 11/724,197, filed on Mar. 15, 2007, which claims priority to European Patent Application No. 06360008.4, filed on Mar. 16, 2006, and European Patent Application No. 06291516.0, filed on Sep. 26, 2006. The entire contents of each of the foregoing applications are expressly incorporated herein by reference.

The present invention relates to compositions and methods for treating ophthalmic disorders of humans or animals. The present compositions and methods are highly suitable for intra- and peri-ocular administration into the interior of an eye and provide therapeutic effects to the eye as they are effective in stabilizing, enhancing and/or improving a patient's vision. More specifically, the present invention relates to compositions and methods for treating ophthalmic diseases or disorders with an exudative and/or inflammatory condition. Even more specifically, the present invention relates to compositions and methods for treating retinal diseases or disorders, and more specifically ophthalmic diseases or disorders related to impaired retinal vessel permeability and/or integrity.

Ophthalmic diseases or disorders in general terms can be divided into (i) front-of-eye diseases or disorders such as, for example, corneal oedema, anterior uveitis, pterygium, corneal diseases or opacifications with an exudative or inflammatory component, conjunctivitis, allergy and laser induced exudation and (ii) back-of-eye diseases or disorders such as, for example, exudative eye diseases and more particularly exudative retinopathies, exudative macular degeneration, macular oedema, diabetic retinopathy, age-related macular degeneration or retinopathy of prematurity.

The pathogenesis of exudative and/or inflammatory eye diseases or disorders, and more particularly of exudative retinopathies, involves blood-retinal barrier (BRB) alteration and inflammation. The retina essentially consists in neuronal matter, and the barrier between the retina and the choroidal vascular system, herein referred as BRB is quite similar to the blood-brain barrier. The BRB is made up of two compartments defined as follows: an inner barrier consisting of retinal vascular endothelial cells that line the blood vessels of the choroid and an outer barrier consisting of the retinal pigment epithelial (RPE) cells that separate the choroid from the retina. Functionally, the BRB is dependent on the integrity of the RPE, the retinal vasculature and associated glial cell layers which behave as an additional component preventing the direct access of blood vessels to the neuronal environment. The BRB functions to preserve the physiological environment of the neuronal retina. When the BRB is compromised, plasma leaks across the BRB into the retina thus contributing to pathological processes such as exudative retinopathies and vision impairment. Ailments associated with breakdown of the BRB in the posterior region of the retina include, for example, oedematous retinal conditions such as, myopic retinopathies, macular oedema such as clinical macular oedema or angiographic cystoid macular oedema arising from various aetiologies such as diabetes, exudative macular degeneration and macular oedema arising for example from laser treatment of the retina.

Other conditions can lead to or be associated with exudative retinopathy. For example, myopic retinopathy is a condition that results from severe malformation of the retina in part due to overgrowth of the sclera. This deformation leads to restriction of the blood vessels network within the choroid, and ultimately to a process of compensatory neovascularisation. Nevertheless, the newly formed vessels appear fragile and prone to leakage and exudation, leading to exudative retinopathy.

Similarly, macular oedema (e.g. clinical macular oedema or angiographic cystoid macular oedema) is a condition involving swelling of the macula and typically occurs as a result of aetiologies such as disease (e.g. diabetes), injury or eye surgery. Fluid collects within the layers of the macula, causing blurred, distorted central vision.

In exudative macular degeneration (also known as "wet" or neovascular age-related macular degeneration (wet-AMD)) abnormal overgrowth of blood vessels from the choroid into the retina occurs, compromising the BRB. The abnormal blood vessels are fragile and prone to leakage.

Diabetic retinopathy is a severe complication of diabetes. In the initial stage, capillary microaneurysm and dot haemorrhage are observed. Thereafter, microvascular obstruction and retinal oedema result from vascular hyperpermeability and neovascularization. In the last stage, retinal detachment is caused by the traction of connective tissues grown in the vitreous body. Further, iris rubeosis and neovascular glaucoma are observed, leading to blindness.

Retinal ischemia or degeneration is another retinopathy. It may result, for example, from injury, trauma, tumours or be associated with various disorders such as occlusion of a blood vessel or elevated intraocular pressure which reduces availability of blood, oxygen or other nutrients to the retina or optic nerve thus leading to neuronal cell death (degeneration) and loss of vision. Such disorders include e.g. diabetes, atherosclerosis, venous capillary insufficiency, obstructive arterial and venous retinopathies (e.g. Retinal Venous Occlusion), glaucoma and senile macular degeneration.

Treatment of such diseases currently focuses on removing or inhibiting vascular growth by laser treatment, drug therapy or a combination of both.

Currently, the most widely used treatment for these disorders is laser therapy which is directed to removal, destruction or blockage of blood vessels via photodynamic therapy or laser photocoagulation. For example, focal laser treatment may be applied to micro-aneurysms identified in diabetic retinopathy. Laser therapy is believed to inhibit neovascularisation and to decrease the extent of oedema. However, a complication of laser treatment is inflammation that may lead to further oedema and destruction of large portion of retina with significant risk of vision alteration. In addition, laser treatment is not always a permanent cure as blood vessels may grow again, and micro-aneurysms may reoccur. Furthermore, laser treatment of abnormal blood vessels cannot be performed on vessels located in certain retinal areas, such as the central region of the macula.

Drug compounds for treating these ophthalmic disorders have been proposed which have anti-angiogenic or angiostatic properties, such as corticosteroid (e.g. anecortave acetate, triamcinolone, . . . ). However, corticosteroids have serious side effects that limit their use, for example increase of intra occular pressure (glaucoma) and cataract formation. Other products are directed against vascular endothelial growth factor (VEGF) such as Lucentis™ also named ranibizumab or Macugen™ also named pegaptanib sodium. However, to date there is insufficient evidence to indicate how successful these compounds will be.

The present invention intends to provide improved compounds and methods for the treatment of ophthalmic disorders that at least slow the rate of development of said ophthalmic disorders and address the principal problem underlying these diseases (i.e. retinal vascular permeability and/or exudation of fluids from vessels and retinal microvessel rupture leading to focal hemorrhages). In one aspect of the present invention, are provided compounds and methods for treating ophthalmic disorders, and more specifically exudative and/or inflammatory ophthalmic disorders. In a more specific aspect of the present invention, are provided compounds and methods for treating back of the eye diseases and/or disorders, and more specifically retinal diseases, and even more specifically ophthalmic disorders related to impaired retinal vessel permeability and/or stability.

In animals, proteases (e.g. kallikrein, plasmin, elastase, urokinase plasminogen activator, thrombin, human lipoprotein-associated coagulation inhibitor or coagulation factors) are involved in a broad range of biological pathways affecting blood flow and are thus essential in wound healing, extracellular matrix destruction, tissue reorganization, and in cascades leading to blood coagulation, fibrinolysis, and complement activation. Proteases are released by inflammatory cells for destruction of pathogens or foreign agents, and by normal and cancerous cells as they move through their surroundings. Overproduction or lack of regulation of proteases activity can have deleterious consequences leading to pathological conditions. For example, kallikreins are serine proteases found in both tissues and plasma, and it has been shown that plasma kallikrein is involved in contact-activated coagulation, fibrinolysis, hypotension, and inflammation (See Bhoola, et al., 1992, Pharmacological Reviews, 44, 1-80).

The activity of proteases is regulated by inhibitors. It has been shown that 10% of the proteins in blood serum are protease inhibitors (Roberts et al., 1995, Critical Reviews in Eukaryotic Gene Expression, 5, 385-436). Inhibitors of proteases, and more particularly of specific serine proteases, therefore have received attention as potential drug targets for various pathological situations, such as ischemic diseases, bleeding episodes (e.g. fibrinolysis or fibrinogenolysis, excessive bleeding associated with thrombolytics, post-operative bleeding and inappropriate androgenesis). One such inhibitor for example, aprotinin (also called bovine pancreatic trypsin inhibitor) has been approved in the United States for prophylactic use in reducing perioperative blood loss and the need for transfusion in patients during coronary artery bypass graft (for a review see Engles, 2005, Am J Health Syst Pharm., 62, S9-14). The effectiveness of aprotinin is actually associated with its relatively non-specific abilities to inhibit a variety of serine proteases, including plasma kallikrein and plasmin. Kallikrein, a serine protease, is an enzyme that initiates the CAS cascade leading to activation of neutrophils, plasmin, coagulation, and various kinins. It is secreted as a zymogen (prekallikrein) that circulates as an inactive molecule until activated by a proteolytic event early in the contact activation cascade.

Protease inhibitors are classified into a series of families based on extensive sequence homologies among the family members and the conservation of intrachain disulfide bridges (for review, see Laskowski and Kato, 1980, Ann. Rev. Biochem. 49, 593-626). Serine protease inhibitors of the Kunitz family (i.e. Kunitz type serine protease inhibitors) are characterized by their homology with aprotinin (bovine pancreatic trypsin inhibitor). The Kunitz type serine protease inhibitors, includes inhibitors of trypsin, chymotrypsin, elastase, kallikrein, plasmin, coagulation factors XIa and IXa, and cathepsin G. These inhibitors thus regulate a variety of physiological processes, including blood coagulation, fibrinolysis, complement activation, inflammation and tumor development. The Kunitz type serine protease inhibitors are generally basic, low molecular weight proteins comprising one or more, native or non native, inhibitory domains ("Kunitz domains"). The Kunitz domain is a folding domain of approximately 50-60 residues, which forms a central anti-parallel beta sheet and a short C-terminal helix (see e.g. U.S. Pat. No. 6,087,473). This characteristic domain comprises six cysteine residues that form three disulfide bonds, resulting in a double-loop structure. Between the N-terminal region and the first beta strand resides the active inhibitory binding loop. This binding loop is disulfide bonded through a Cys residue to the hairpin loop formed between the last two beta strands. Isolated Kunitz domains from a variety of proteinase inhibitors display an inhibitory activity (e.g., Petersen et al., 1996, Eur. J. Biochem. 125, 310-316; Wagner et al., 1992, Biochem. Biophys. Res. Comm. 186, 1138-1145). Linked Kunitz domains also have an inhibitory activity (see for example U.S. Pat. No. 6,087,473). Proteinase inhibitors comprising one or more Kunitz domains include tissue factor pathway inhibitor (TFPI), tissue factor pathway inhibitor 2 (TFPI-2), amyloid β-protein precursor (AβPP), aprotinin, and placental bikunin.

The present invention is based on the discovery that inhibitors of serine proteases, such as, for example, kallikrein, can successfully be employed to treat ophthalmic disorders, and more specifically exudative and/or inflammatory ophthalmic disorders. According to one special embodiment, said inhibitors are peptides that inhibit serine proteases, such as, for example, kallikrein. Similarly, it has been shown that said inhibitors (e.g. said peptides) can successfully be employed to treat back of the eye diseases, and more specifically diseases related to impaired retinal vessel permeability and/or integrity (e.g. retinal degeneration). More specifically, the invention provides methods of using kallikrein inhibitors in a method for treating and/or preventing ophthalmic disorders and compositions for such use. The invention also relates to methods for reducing, inhibiting or preventing exudative and/or inflammatory conditions in the eye, and more particularly in the back of the eye and compositions for such use.

According to a first embodiment, the Invention provides an ophthalmic composition useful for intraocular placement in an eye of a patient comprising a therapeutically effective amount of at least one peptide that inhibits serine protease and an ophthalmically compatible solvent component.

According to another embodiment, said ophthalmic composition further comprises a biocompatible polymeric component in an amount effective to delay release of the said peptide into the interior of the eye after the composition is intraocularly placed in the eye; and an ophthalmically compatible solvent component in an amount effective to solubilize the polymeric component, the composition being effective, after being intraocularly placed into the interior of the eye, to form a delayed release composition effective to delay the release of the said peptide in the eye relative to intraocular placement of a substantially identical composition without the polymeric component.

According to another embodiment, the present invention relates to a method for the prophylactic or therapeutic treatment of ophthalmic disorders in a patient in need of such treatment that comprises the step of administering a composition comprising a therapeutically effective amount of at least one peptide that inhibits serine protease in said patient.

According to another embodiment, the present invention relates to a method for reducing, inhibiting or preventing exudative and/or inflammatory conditions in the eye, and more particularly in the back of the eye and compositions for such use, wherein said method comprises the step of administering a composition comprising a therapeutically effective amount of at least one peptide that inhibits serine protease in a patient in need thereof.

According to another embodiment, the present invention relates to the use of at least one peptide that inhibits serine protease for the preparation of an ophthalmic composition useful for the prophylactic or therapeutic treatment of ophthalmic disorders in a patient, and more specifically those cited above.

According to one specific embodiment, said serine protease in all the above is kallikrein.

According to another specific embodiment, said serine protease in all the above is plasma kallikrein.

According to another specific embodiment, said peptides of the Invention that inhibits serine protease are kallikrein inhibitors, more preferably Kunitz domain polypeptides.

According to one specific embodiment, said peptide of the Invention that inhibits serine protease includes (or consists of) the amino acid sequence:

Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), or a fragment or variant thereof, e.g. a fragment that binds and inhibits kallikrein. For example, the peptide can have fewer than 80, 70, 65, 60, 58, 55 or 52 amino acids.

"$Xaa_s$" refers to positions in a peptide sequence and are, independently from one another, any amino acid.

According to a specific embodiment, Xaa can by any amino acid except cysteine.

According to other specific embodiments, one or more of the following apply:

Xaa1, Xaa2, Xaa3, Xaa4, Xaa56, Xaa57 or Xaa58 are, independently from one another, any amino acid or absent;

Xaa10 is an amino acid selected from the group consisting of Asp and Glu;

Xaa11 is an amino acid selected from the group consisting of Asp, Gly, Ser, Val, Asn, Ile, Ala and Thr;

Xaa13 is an amino acid selected from the group consisting of Arg, His, Pro, Asn, Ser, Thr, Ala, Gly, Lys and Gln;

Xaa15 is an amino acid selected from the group consisting of Arg, Lys, Ala, Ser, Gly, Met, Asn and Gln;

Xaa16 is an amino acid selected from the group consisting of Ala, Gly, Ser, Asp and Asn;

Xaa17 is an amino acid selected from the group consisting of Ala, Asn, Ser, Ile, Gly, Val, Gln and Thr;

Xaa18 is an amino acid selected from the group consisting of His, Leu, Gln and Ala;

Xaa19 is an amino acid selected from the group consisting of Pro, Gln, Leu, Asn and Ile;

Xaa21 is an amino acid selected from the group consisting of Trp, Phe, Tyr, His and Ile;

Xaa22 is an amino acid selected from the group consisting of Tyr and Phe;

Xaa23 is an amino acid selected from the group consisting of Tyr and Phe;

Xaa31 is an amino acid selected from the group consisting of Glu, Asp, Gln, Asn, Ser, Ala, Val, Leu, Ile and Thr;

Xaa32 is an amino acid selected from the group consisting of Glu, Gln, Asp Asn, Pro, Thr, Leu, Ser, Ala, Gly and Val;

Xaa34 is an amino acid selected from the group consisting of Thr, Ile, Ser, Val, Ala, Asn, Gly and Leu;

Xaa35 is an amino acid selected from the group consisting of Tyr, Trp and Phe;

Xaa39 is an amino acid selected from the group consisting of Glu, Gly, Ala, Ser and Asp;

Xaa40 is an amino acid selected from the group consisting of Gly and Ala;

Xaa43 is an amino acid selected from the group consisting of Asn and Gly;

Xaa45 is an amino acid selected from the group consisting of Phe and Tyr;

Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 are, independently from one another, any amino acid.

According to another specific embodiment, each of the first and/or last four amino acids of SEQ ID NO:1 can optionally be present or absent and can be any amino acid, if present, e.g., any non-cysteine amino acid.

According to another specific embodiment, each of the first and/or last three amino acids of SEQ ID NO:1 can optionally be present or absent and can be any amino acid, if present, e.g., any non-cysteine amino acid.

According to another specific embodiment, it is possible to remove one, two, three, or four amino acids from the N-terminus of an amino acid sequence described herein, and/or one, two, three, four, or five amino acids from the C-terminus of an amino acid sequence described herein.

According to another specific embodiment, the peptide of the Invention has a sequence with one or more of the following properties: Xaa11 is an amino acid selected from the group consisting of Asp, Gly, Ser or Val; Xaa13 is an amino acid selected from the group consisting of Pro, Arg, His or Asn; Xaa15 is an amino acid selected from the group consisting of Arg or Lys; Xaa16 is an amino acid selected from the group consisting of Ala or Gly; Xaa17 is an amino acid selected from the group consisting of Ala, Asn, Ser or Ile; Xaa18 is an amino acid selected from the group consisting of His, Leu or Gln; Xaa19 can be Pro, Gln or Leu; Xaa21 is an amino acid selected from the group consisting of Trp or Phe; Xaa31 is Glu; Xaa32 is an amino acid selected from the group consisting of Glu or Gln; Xaa34 is an amino acid selected from the group consisting of Ile, Thr or Ser; Xaa35 is Tyr; and Xaa39 is an amino acid selected from the group consisting of Glu, Gly or Ala.

According to another specific embodiment, the peptide of the Invention includes the following amino acids: Xaa10 is Asp; Xaa11 is Asp; Xaa13 is an amino acid selected from the group consisting of Pro or Arg; Xaa15 is Arg; Xaa16 is an amino acid selected from the group consisting of Ala or Gly; Xaa17 is Ala; Xaa18 is His; Xaa19 is Pro; Xaa21 is Trp; Xaa31 is Glu; Xaa32 is Glu; Xaa34 is an amino acid selected from the group consisting of Ile or Ser; Xaa35 is Tyr; and Xaa39 is Gly.

According to the present Invention, it is possible to use all or part of the peptides described herein. For example, peptides of the Invention can include binding domains for specific kallikrein epitopes. For example, the binding loops of Kunitz domains can be cyclized and used in isolation or can be grafted onto another domain, e.g., a framework of another Kunitz domain.

Examples of peptides according to the present Invention are described by the following (where not indicated, "Xaa" refers to any amino acid, any non-cysteine amino acid or any amino acid from the same set of amino acids that are allowed for SEQ ID NO:1):

(SEQ ID NO: 2)
Met His Ser Phe Cys Ala Phe Lys Ala Asp Asp Gly Pro Cys Arg Ala
Ala His Pro Arg Trp Phe Phe Asn Ile Phe Thr Arg Gln Cys Glu Glu Phe
Ile Tyr Gly Gly Cys Glu Gly Asn Gln Asn Arg Phe Glu Ser Leu Glu Glu
Cys Lys Lys Met Cys Thr Arg Asp, (SEQ ID NO: 3)
Met His Ser Phe Cys Ala Phe Lys Ala Xaa10 Xaa11 Gly Xaa13 Cys
Xaa15 Xaa16 Xaa17 Xaa18 Xaa19 Arg Xaa21 Phe Phe Asn Ile Phe Thr Arg
Gln Cys Xaa31 Xaa32 Phe Xaa34 Xaa35 Gly Gly Cys Xaa39 Gly Asn Gln
Asn Arg Phe Glu Ser Leu Glu Glu Cys Lys Lys Met Cys Thr Arg Asp, (SEQ ID NO: 4)
Met His Ser Phe Cys Ala Phe Lys Ala Asp Asp Gly Pro Cys Lys Ala
Asn His Leu Arg Phe Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 5)
Met His Ser Phe Cys Ala Phe Lys Ala Asp Asp Gly His Cys Lys Ala
Asn His Gln Arg Phe Phe Asn Ile Phe Thr Arg Gln Cys Glu Glu Phe
Thr Tyr Gly Gly Cys Gly Gly Asn Gln Asn Arg Phe Glu Ser Leu Glu Glu
Cys Lys Lys Met Cys Thr Arg Asp, (SEQ ID NO: 6)
Met His Ser Phe Cys Ala Phe Lys Ala Asp Asp Gly His Cys Lys Ala
Asn His Gln Arg Phe Phe Phe Asn Ile Phe Thr Arg Gln Cys Glu Gln Phe
Thr Tyr Gly Gly Cys Ala Gly Asn Gln Asn Arg Phe Glu Ser Leu Glu Glu
Cys Lys Lys Met Cys Thr Arg Asp, (SEQ ID NO: 7)
Met His Ser Phe Cys Ala Phe Lys Ala Asp Asp Gly His Cys Lys Ala
Ser Leu Pro Arg Phe Phe Phe Asn Ile Phe Thr Arg Gln Cys Glu Glu Phe
Ile Tyr Gly Gly Cys Gly Gly Asn Gln Asn Arg Phe Glu Ser Leu Glu Glu
Cys Lys Lys Met Cys Thr Arg Asp, (SEQ ID NO: 8)
Met His Ser Phe Cys Ala Phe Lys Ala Asp Asp Gly His Cys Lys Ala
Asn His Gln Arg Phe Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 9)
Met His Ser Phe Cys Ala Phe Lys Ala Asp Asp Gly His Cys Lys Gly
Ala His Leu Arg Phe Phe Phe Asn Ile Phe Thr Arg Gln Cys Glu Glu Phe
Ile Tyr Gly Gly Cys Glu Gly Asn Gln Asn Arg Phe Glu Ser Leu Glu Glu
Cys Lys Lys Met Cys Thr Arg Asp, (SEQ ID NO: 10)
Met His Ser Phe Cys Ala Phe Lys Ala Asp Asp Gly Arg Cys Lys Gly
Ala His Leu Arg Phe Phe Phe Asn Ile Phe Thr Arg Gln Cys Glu Glu Phe
Ile Tyr Gly Gly Cys Glu Gly Asn Gln Asn Arg Phe Glu Ser Leu Glu Glu
Cys Lys Lys Met Cys Thr Arg Asp,

-continued (SEQ ID NO: 11)
Met His Ser Phe Cys Ala Phe Lys Ala Asp Gly Gly Arg Cys Arg Gly
Ala His Pro Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 12)
et His Ser Phe Cys Ala Phe Lys Ala Asp Asp Gly Pro Cys Arg Ala
Ala His Pro Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 13)
Met His Ser Phe Cys Ala Phe Lys Ala Asp Val Gly Arg Cys Arg Gly
Ala His Pro Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 14)
Met His Ser Phe Cys Ala Phe Lys Ala Asp Val Gly Arg Cys Arg Gly
Ala Gln Pro Arg Phe Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 15)
Met His Ser Phe Cys Ala Phe Lys Ala Asp Gly Ser Cys Arg Ala
Ala His Leu Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 16)
Met His Ser Phe Cys Ala Phe Lys Ala Glu Gly Gly Ser Cys Arg Ala
Ala His Gln Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 17)
Met His Ser Phe Cys Ala Phe Lys Ala Asp Asp Gly Pro Cys Arg Gly
Ala His Leu Arg Phe Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 18)
Met His Ser Phe Cys Ala Phe Lys Ala Asp Asp Gly His Cys Arg Gly
Ala Leu Pro Arg Trp Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp, (SEQ ID NO: 19)
Met His Ser Phe Cys Ala Phe Lys Ala Asp Ser Gly Asn Cys Arg Gly
Asn Leu Pro Arg Phe Phe Phe Asn Ile Phe Thr Arg Gln Cys Glu Glu Phe
Ser Tyr Gly Gly Cys Gly Gly Asn Gln Asn Arg Phe Glu Ser Leu Glu Glu
Cys Lys Lys Met Cys Thr Arg Asp,

```
                                                         (SEQ ID NO: 20)
Met His Ser Phe Cys Ala Phe Lys Ala Asp Ser Gly Arg Cys Arg Gly

Asn His Gln Arg Phe Phe Asn Ile Phe Thr Arg Gln Cys Glu Glu Phe

Ser Tyr Gly Gly Cys Gly Gly Asn Gln Asn Arg Phe Glu Ser Leu Glu Glu

Cys Lys Lys Met Cys Thr Arg Asp, (SEQ ID NO: 21)
Met His Ser Phe Cys Ala Phe Lys Ala Asp Gly Gly Arg Cys Arg Ala

Ile Gln Pro Arg Trp Phe Phe Asn Ile Phe Thr Arg Gln Cys Glu Glu Phe

Ser Tyr Gly Gly Cys Gly Gly Asn Gln Asn Arg Phe Glu Ser Leu Glu Glu

Cys Lys Lys Met Cys Thr Arg Asp, (SEQ ID NO: 22)
Met His Ser Phe Cys Ala Phe Lys Ala Asp Asp Gly Arg Cys Arg Gly

Ala His Pro Arg Trp Phe Phe Asn Ile Phe Thr Arg Gln Cys Glu Glu Phe

Ser Tyr Gly Gly Cys Gly Gly Asn Gln Asn Arg Phe Glu Ser Leu Glu Glu

Cys Lys Lys Met Cys Thr Arg Asp.
```

Additional examples of peptides according to the present Invention are those that differ (e.g., substitutions, insertions, or deletions) by at least one amino acid, but fewer than seven, six, five, four, three, or two amino acids differences relative to an amino acid sequence described herein, e.g., an amino acid sequence provided above. In one embodiment, fewer than three, two, or one differences are in one of the binding loops. For example, the first binding loop may have no differences relative to an amino acid sequence described herein, e.g., an amino acid sequence provided above. In another example, neither the first nor the second binding loop differs from an amino acid sequence described herein, e.g., an amino acid sequence provided above.

The peptide of the present invention can include (or consist of) a polypeptide described in U.S. Pat. No. 5,786,328, U.S. Pat. No. 6,333,402 or U.S. Pat. No. 6,010,880, the content of which is incorporated by reference.

Examples of peptides according to the present Invention are described by the following (where not indicated, "Xaa" refers to any amino acid, any non-cysteine amino acid or any amino acid from the same set of amino acids that are allowed for SEQ ID NO:1):

```
                                                         (SEQ ID NO: 23)
Glu Ala Met His Ser Phe Cys Ala Phe Lys Ala Asp Asp Gly Pro Cys

Arg Ala Ala His Pro Arg Trp Phe Phe Asn Ile Phe Thr Arg Gln Cys Glu

Glu Phe Ile Tyr Gly Gly Cys Glu Gly Asn Gln Asn Arg Phe Glu Ser Leu

Glu Glu Cys Lys Lys Met Cys Thr Arg Asp, (SEQ ID NO: 24)
Glu Ala Met His Ser Phe Cys Ala Phe Lys Ala Xaa10 Xaa11 Gly

Xaa13 Cys Xaa15 Xaa16 Xaa17 Xaa18 Xaa19 Arg Xaa21 Phe Phe Asn Ile

Phe Thr Arg Gln Cys Xaa31 Xaa32 Phe Xaa34 Xaa35 Gly Gly Cys Xaa39

Gly Asn Gln Asn Arg Phe Glu Ser Leu Glu Glu Cys Lys Lys Met Cys Thr

Arg Asp, (SEQ ID NO: 25)
Glu Ala Met His Ser Phe Cys Ala Phe Lys Ala Asp Asp Gly Pro Cys

Lys Ala Asn His Leu Arg Phe Phe Asn Ile Phe Thr Arg Gln Cys Glu

Glu Phe Ser Tyr Gly Gly Cys Gly Gly Asn Gln Asn Arg Phe Glu Ser Leu

Glu Glu Cys Lys Lys Met Cys Thr Arg Asp, (SEQ ID NO: 26)
Glu Ala Met His Ser Phe Cys Ala Phe Lys Ala Asp Asp Gly His Cys

Lys Ala Asn His Gln Arg Phe Phe Asn Ile Phe Thr Arg Gln Cys Glu
```

```
                                        -continued

Glu Phe Thr Tyr Gly Gly Cys Gly Gly Asn Gln Asn Arg Phe Glu Ser Leu

Glu Glu Cys Lys Lys Met Cys Thr Arg Asp, (SEQ ID NO: 27)
Glu Ala Met His Ser Phe Cys Ala Phe Lys Ala Asp Asp Gly His Cys

Lys Ala Asn His Gln Arg Phe Phe Phe Asn Ile Phe Thr Arg Gln Cys Glu

Gln Phe Thr Tyr Gly Gly Cys Ala Gly Asn Gln Asn Arg Phe Glu Ser Leu

Glu Glu Cys Lys Lys Met Cys Thr Arg Asp, (SEQ ID NO: 28)
Glu Ala Met His Ser Phe Cys Ala Phe Lys Ala Asp Asp Gly His Cys

Lys Ala Ser Leu Pro Arg Phe Phe Phe Asn Ile Phe Thr Arg Gln Cys Glu

Glu Phe Ile Tyr Gly Gly Cys Gly Gly Asn Gln Asn Arg Phe Glu Ser Leu

Glu Glu Cys Lys Lys Met Cys Thr Arg Asp, (SEQ ID NO: 29)
Glu Ala Met His Ser Phe Cys Ala Phe Lys Ala Asp Asp Gly His Cys

Lys Ala Asn His Gln Arg Phe Phe Phe Asn Ile Phe Thr Arg Gln Cys Glu

Glu Phe Ser Tyr Gly Gly Cys Gly Gly Asn Gln Asn Arg Phe Glu Ser Leu

Glu Glu Cys Lys Lys Met Cys Thr Arg Asp, (SEQ ID NO: 30)
Glu Ala Met His Ser Phe Cys Ala Phe Lys Ala Asp Asp Gly His Cys

Lys Gly Ala His Leu Arg Phe Phe Phe Asn Ile Phe Thr Arg Gln Cys Glu

Glu Phe Ile Tyr Gly Gly Cys Glu Gly Asn Gln Asn Arg Phe Glu Ser Leu

Glu Glu Cys Lys Lys Met Cys Thr Arg Asp, (SEQ ID NO: 31)
Glu Ala Met His Ser Phe Cys Ala Phe Lys Ala Asp Asp Gly Arg Cys

Lys Gly Ala His Leu Arg Phe Phe Phe Asn Ile Phe Thr Arg Gln Cys Glu

Glu Phe Ile Tyr Gly Gly Cys Glu Gly Asn Gln Asn Arg Phe Glu Ser Leu

Glu Glu Cys Lys Lys Met Cys Thr Arg Asp, (SEQ ID NO: 32)
Glu Ala Met His Ser Phe Cys Ala Phe Lys Ala Asp Gly Gly Arg Cys

Arg Gly Ala His Pro Arg Trp Phe Phe Asn Ile Phe Thr Arg Gln Cys Glu

Glu Phe Ser Tyr Gly Gly Cys Gly Gly Asn Gln Asn Arg Phe Glu Ser Leu

Glu Glu Cys Lys Lys Met Cys Thr Arg Asp, (SEQ ID NO: 33)
Glu Ala Met His Ser Phe Cys Ala Phe Lys Ala Asp Asp Gly Pro Cys

Arg Ala Ala His Pro Arg Trp Phe Phe Asn Ile Phe Thr Arg Gln Cys Glu

Glu Phe Ser Tyr Gly Gly Cys Gly Gly Asn Gln Asn Arg Phe Glu Ser Leu

Glu Glu Cys Lys Lys Met Cys Thr Arg Asp, (SEQ ID NO: 34)
Glu Ala Met His Ser Phe Cys Ala Phe Lys Ala Asp Val Gly Arg Cys

Arg Gly Ala His Pro Arg Trp Phe Phe Asn Ile Phe Thr Arg Gln Cys Glu

Glu Phe Ser Tyr Gly Gly Cys Gly Gly Asn Gln Asn Arg Phe Glu Ser Leu

Glu Glu Cys Lys Lys Met Cys Thr Arg Asp, (SEQ ID NO: 35)
Glu Ala Met His Ser Phe Cys Ala Phe Lys Ala Asp Val Gly Arg Cys

Arg Gly Ala Gln Pro Arg Phe Phe Phe Asn Ile Phe Thr Arg Gln Cys Glu
```

-continued

```
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 36)
Glu Ala Met His Ser Phe Cys Ala Phe Lys Ala Asp Asp Gly Ser Cys
Arg Ala Ala His Leu Arg Trp Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 37)
Glu Ala Met His Ser Phe Cys Ala Phe Lys Ala Glu Gly Gly Ser Cys
Arg Ala Ala His Gln Arg Trp Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 38)
Glu Ala Met His Ser Phe Cys Ala Phe Lys Ala Asp Asp Gly Pro Cys
Arg Gly Ala His Leu Arg Phe Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 39)
Glu Ala Met His Ser Phe Cys Ala Phe Lys Ala Asp Asp Gly His Cys
Arg Gly Ala Leu Pro Arg Trp Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 40)
Glu Ala Met His Ser Phe Cys Ala Phe Lys Ala Asp Ser Gly Asn Cys
Arg Gly Asn Leu Pro Arg Phe Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Net Cys Thr Arg Asp, (SEQ ID NO: 41)
Glu Ala Met His Ser Phe Cys Ala Phe Lys Ala Asp Ser Gly Arg Cys
Arg Gly Asn His Gln Arg Phe Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 42)
Glu Ala Met His Ser Phe Cys Ala Phe Lys Ala Asp Gly Gly Arg Cys
Arg Ala Ile Gln Pro Arg Trp Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp, (SEQ ID NO: 43)
Glu Ala Met His Ser Phe Cys Ala Phe Lys Ala Asp Asp Gly Arg Cys
Arg Gly Ala His Pro Arg Trp Phe Phe Asn Ile Phe Thr Arg Gln Cys Glu
Glu Phe Ser Tyr Gly Gly Cys Gly Gly Asn Gln Asn Arg Phe Glu Ser Leu
Glu Glu Cys Lys Lys Met Cys Thr Arg Asp.
```

According to another embodiment, said peptide of the Invention that inhibits serine protease includes (or consists of) the amino acid sequence:

Xaa-1 Xaa0 Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:44), or a fragment or variant thereof, e.g. a fragment that binds and inhibits kallikrein wherein Xaa1 to Xaa58 are as defined above and Xaa-1 is Glu and Xaa0 is Ala.

According to preferred embodiment, the peptide of the Invention is SEQ ID NO:23 (Markland et al., 1996, Biochemistry, 35, 8058-8067; Ley et al., 1996, Mol Divers, 2, 119-124; U.S. Pat. No. 6,333,402).

The present invention also extends to the use of variants of the above disclosed peptides, said variants being more specifically defined as substantially homologous to the peptides above disclosed. The term "substantially homologous", when used in connection with amino acid sequences, refers to sequences which are substantially identical to or similar in sequence, giving rise to a homology in conformation and thus to similar biological activity. The term is not intended to imply a common evolution of the sequences. Typically, "substantially homologous" sequences are at least 50% more preferably at least 80% identical in sequence, at least over any regions known to be involved in the desired activity. Most preferably, no more than five residues, other than at the termini, are different. Preferably, the divergence in sequence, at least in the aforementioned regions, is in the form of "conservative modifications". "Conservative modifications" are defined as (i) conservative substitutions of amino acids as hereafter defined; and (ii) single or multiple insertions or deletions of amino acids at the termini, at interdomain boundaries, in loops or in other segments of relatively high mobility (as indicated, e.g., by the failure to clearly resolve their structure upon X-ray diffraction analysis or NMR). Preferably, except at the termini, no more than about five amino acids are inserted or deleted at a particular locus, and the modifications are outside regions known to contain binding sites important to activity. Conservative substitutions are herein defined as exchanges within one of the following five groups:

I. Small aliphatic, nonpolar or slightly polar residues: Ala, Ser, Thr (Pro, Gly)
II. Polar, negatively charged residues: and their amides Asp, Asn, Glu, Gln
III. Polar, positively charged residues: His, Arg, Lys
IV. Large, aliphatic, nonpolar residues: Met, Leu, Ile, Val (Cys)
V. Large, aromatic residues: Phe, Tyr, Trp.

Residues Pro, Gly and Cys are parenthesized because they have special conformational roles. Cys participates in formation of disulfide bonds. Gly imparts flexibility to the chain. Pro imparts rigidity to the chain and disrupts alpha helices. These residues may be essential in certain regions of the polypeptide, but substitutable elsewhere.

Semi-conservative substitutions are defined to be exchanges between two of groups (I)-(V) above which are limited to supergroup (a), comprising (I), (II) and (III) above, or to supergroup (B), comprising (IV) and (V) above.

The compounds are not limited to the side groups found in genetically encoded amino acids; rather, conservative substitutions are allowed. Lys can be replaced by Arg, ornithine, guanidolysine, and other side groups that carry a positive charge. Asn can be replaced by other small, neutral, hydrophilic groups, such as (but without limitation) Ser, O-methyl serine, Gln, alpha-amidoglycine, Ala, alpha-aminobutyric acid, and alpha-amino-gamma-hydroxybutyric acid (homoserine). His could be replaced with other amino acids having one or more of the properties: amphoteric, aromatic, hydrophobic, and cyclic. For example (without limitation), His could be replaced with methylhistidine, L-p-aminophenylalanine, L-m-(N,N,dimethylamino)phenylalanine, canavanine and N-methylasparagine.

The Kunitz domains are quite small; if this should cause a pharmacological problem, such as excessively quick elimination from the circulation, two or more such domains may be joined by a linker. This linker is preferably a sequence of one or more amino acids. Peptide linkers have the advantage that the entire protein may then be expressed by recombinant DNA techniques. It is also possible to use a non-peptidyl linker, such as one of those commonly used to form immunogenic conjugates.

Chemical polypeptide synthesis is a well-described and practiced in the art. In general, as is known in the art, such methods involve blocking or protecting reactive functional groups, such as free amino, carboxyl and thio groups. After polypeptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

The term "and/or" wherever used in the present Invention includes the meaning of "and", "or" and "all or any other combination of the elements connected by said term".

The terms "amino acids" and "residues" are synonyms and encompass natural amino acids as well as amino acid analogs (e.g. non-natural, synthetic and modified amino acids, including D or L optical isomers).

The terms "polypeptide", "peptide" and "protein" are used herein interchangeably to refer to polymers of amino acid residues which comprise ten or more amino acids bonded via peptide bonds. The polymer can be linear, branched or cyclic and may comprise naturally occurring and/or amino acid analogs and it may be interrupted by non-amino acids. As a general indication, if the amino acid polymer is long (e.g. more than 50 amino acid residues), it is preferably referred to as a polypeptide or a protein.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

According to a specific embodiment, the peptides of the present invention are PEGylated, i.e. a plurality of polyethylene glycol moieties are attached to the said peptide, especially those peptides that present available lysines and an N-terminus for modification with mPEG (see US20050089515).

According to a specific embodiment, the ophthalmic disorders of the present invention are exudative and/or inflammatory ophthalmic disorders.

According to a specific embodiment, the ophthalmic disorders of the present invention are disorders related to impaired retinal vessel permeability and/or integrity.

According to another specific embodiment, the ophthalmic disorders of the present invention are disorders related to retinal microvessel rupture leading to focal hemorrhages.

According to another embodiment, the ophthalmic disorders of the present invention are back of the eye diseases, and more specifically retinal diseases.

According to another embodiment, the ophthalmic disorders of the present invention are front of the eye diseases.

According to the present Invention the terms "disease" and "disorder" have the same meaning.

Among the ophthalmic disorders (including exudative and/or inflammatory ophthalmic disorders, disorders related to impaired retinal vessel permeability and/or integrity, disorders related to retinal microvessel rupture leading to focal hemorrhages, back of the eye diseases, retinal diseases, and front of the eye diseases) which can be treated or addressed in accordance with the present invention include, without limitation, the following: Age Related Macular Degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, Acute Macular Neuroretinopathy, Central Serous Chorioretinopathy, chorioretinopathy, Choroidal Neovascularization, neovascular maculopathy, neovascular glaucoma, obstructive arterial and venous retinopathies (e.g. Retinal Venous Occlusion or Retinal Arterial Occlusion), Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angitis, Sickle Cell Retinopathy and other Hemoglobinopathies, Angioid Streaks, macular oedema occurring as a result of aetiologies such as disease (e.g. Diabetic Macular Oedema), eye injury or eye surgery; retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, an ocular inflammatory disease caused by bacterial or viral infection, and by an ophthalmic operation, an ocular inflammatory disease caused by a physical injury to the eye, a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

According to the present invention, the term "back-of-eye diseases" refers to diseases affecting among other the retina, macular, fovea in the posterior region of the eye. Examples of back-of-eye disease include macular oedema such as clinical macular oedema or angiographic cystoid macular oedema arising from various aetiologies such as diabetes, exudative macular degeneration and macular oedema arising from laser treatment of the retina, age-related macular degeneration, retinopathy of prematurity (also known as retrolental fibroplasia), retinal ischemia and choroidal neovascularization, retinal diseases (diabetic retinopathy, diabetic retinal oedema, retinal detachment, senile macular degeneration due to sub-retinal neovascularization, myopic retinopathy); inflammatory diseases; uveitis associated with neoplasms such as retinoblastoma or pseudoglioma; neovascularization following vitrectomy; vascular diseases (retinal ischemia, choroidal vascular insufficiency, choroidal thrombosis, retinopathies resulting from carotid artery ischemia); neovascularization of the optic nerve.

According to the present invention, the term "front-of-eye" diseases refers to diseases affecting predominantly the tissues at the front-of-eye, such as the cornea, iris, ciliary body, conjunctiva etc. Examples of front-of-eye diseases include corneal neovascularization (due to inflammation, transplantation, developmental hypoplasia of the iris, corneal diseases or opacifications with an exudative or inflammatory component, neovascularization due to penetration of the eye or contusive ocular injury; chronic uveitis; anterior uveitis; inflammatory conditions resulting from surgeries such as LASIK, LASEK, refractive surgery, IOL implantation; irreversible corneal oedema as a complication of cataract surgery; oedema as a result of insult or trauma (physical, chemical, pharmacological, etc); inflammation; conjunctivitis (eg. persistent allergic, giant papillary, seasonal intermittent allergic, perennial allergic, toxic, conjunctivitis caused by infection by bacteria, viruses or Chlamydia); keratoconjunctivitis (vernal, atopic, Sicca); iridocyclitis; iritis; scleritis; episcleritis; infectious keratitis; superficial punctuate keratitis; keratoconus; posterior polymorphous dystrophy; Fuch's dystrophies (corneal and endothelial); aphakic and pseudophakic bullous keratopathy; corneal oedema; scleral disease; ocular cicatrcial pemphigoid; pars planitis; Posner Schlossman syndrome; Behget's disease; Vogt-Koyanagi-Harada syndrome; hypersensitivity reactions; ocular surface disorders; conjunctival oedema; Toxoplasmosis chorioretinitis; inflammatory pseudotumor of the orbit; chemosis; conjunctival venous congestion; periorbital cellulitis; acute dacryocystitis; non-specific vasculitis; sarcoidosis; cytomegalovirus infection.

In preferred embodiment, the Invention concerns back of the eye diseases.

According to the present invention, the term "therapeutically effective amount" is used herein to refer to an amount of therapeutic agent either as an individual compound or in combination with other compounds that is sufficient to induce a therapeutic effect on the ailment which the compound is applied to. This phrase should not be understood to mean that the dose must completely eradicate the ailment. What constitutes a therapeutically effective amount will vary depending on, inter alia, the biopharmacological properties of the compound used in the methodology, the condition being treated, the frequency of administration, the mode of delivery, characteristics of the individual to be treated the severity of the disease and the response of the patient. These are the types of factors that a skilled pharmaceutical chemist will be aware of and will be able to account for when formulating compositions for a treatment as described herein.

An effective quantity of the peptide of interest is preferably employed in the method of the invention. For ocular and extraocular formulations, the concentration of the peptide may be in the range of about 0.01% w/w to about 10% w/w. Typically, the concentration for this mode of delivery is in the range of about 0.025% w/w to about 2.5% w/w.

The precise pharmaceutical formulation (i.e. ophthalmic composition) used in the method of the present invention will vary according to a wide range of commercial and scientific criteria. That is the skilled reader will appreciate that the above formulation of the invention described above may contain other agents.

For example, the ophthalmic compositions used in the methods of the invention are preferably prepared using a physiological saline solution as a vehicle. The pH of the ophthalmic composition may be maintained at a substantially neutral pH (for example, about 7.4, in the range of about 6. 5 to about 7.4, etc.) with an appropriate buffer system as known to one skilled in the art (for example, acetate buffers, citrate buffers, phosphate buffers, borate buffers).

Any diluent used in the preparation of the ophthalmic composition may preferably be selected so as not to unduly affect the biological activity of the composition. Examples of such diluents which are especially useful for injectable ophthalmic composition are water, the various saline, organic or inorganic salt solutions, Ringer's solution, dextrose solution, and Hank's solution.

In addition, the ophthalmic composition used in the method of the invention may include additives such as other buffers, diluents, carriers, adjuvants or excipients. Any pharmacologically acceptable buffer suitable for application to the eye may be used, e.g., tris or phosphate buffers. Other agents may be employed in the formulation for a variety of purposes. For example, buffering agents, preservatives, co-solvents, surfactants, oils, humectants, emollients, chelating agents, stabilizers or antioxidants may be employed. Water soluble preservatives which may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. A surfactant may be Tween 80.

Other vehicles that may be used include, but are not limited to, polyvinyl alcohol, povidone, hydroxypropyl methyl cellulose, poloxamers, carboxymethyl cellulose, hydroxyethyl cellulose, purified water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylated hydroxyanisole, butylated hydroxytoluene, etc. The indications, effective doses, formulations, contraindications, vendors etc, of the compounds in the ophthalmic composition are available or are known to one skilled in the art.

These agents may be present in individual amounts of from about 0.001% to about 5% by weight and preferably about 0.01% to about 2%. Suitable water soluble buffering agents that may be employed are sodium carbonate, sodium borate, sodium phosphate, sodium acetate, sodium bicarbonate, etc., as approved by the US FDA for the desired route of administration. These agents may be present in amounts sufficient to maintain a pH of the system of between about 2 to about 9 and preferably about 4 to about 8. As such, the buffering agent may be as much as about 5% (w/w) of the total ophthalmic composition. Electrolytes such as, but not limited to, sodium chloride and potassium chloride may also be included in the formulation.

The ophthalmic composition of the present invention for the treatment or prevention of ophthalmic disorders may be provided in the form of a single unit dose in a pre-prepared syringe, ready for administration.

In performing the method of the invention, ophthalmic composition may be administered to a patient by any method that leads to delivery of the therapeutic agent (i.e. the peptide of the Invention) to the site of the ophthalmic condition (e.g. the location of an exudative retinopathy, inflammation or macular oedema). Any of the ophthalmic composition may be administered by an ocular route, such as topical, subconjunctival, sub-Tenon, intraocular, ocular implants etc.

Administration of the ophthalmic composition to perform the method of the invention is preferably by intraocular injection, although other modes of administration may be effective. Typically, ophthalmic composition will be delivered intraocularly (by chemical delivery system or invasive device) to an individual. However, the invention is not limited to intraocular delivery in that it also includes topically (extraocular application) or systemically (e.g. oral or other parenteral route such as for example subcutaneous administration) provided that a sufficient amount of the peptide within cells or tissue located in an eye or adjacent an eye achieves contact with the site of the ophthalmic condition. Parenteral administration is used in appropriate circumstances apparent to the practitioner. Preferably, the ophthalmic compositions are administered in unit dosage forms suitable for single administration of precise dosage amounts.

As mentioned above, delivery to areas within the eye, in situ can be accomplished by injection, cannula or other invasive device designed to introduce precisely metered amounts of a desired ophthalmic composition to a particular compartment or tissue within the eye (e.g. posterior chamber or retina). An intraocular injection may be into the vitreous (intravitreal), or under the conjunctiva (subconjunctival), or behind the eye (retrobulbar), into the sclera, or under the Capsule of Tenon (sub-Tenon), and may be in a depot form. Other intraocular routes of administration and injection sites and forms are also contemplated and are within the scope of the invention.

Preferably, the intraocular injection is an intravitreal injection, preferably through self sealing gauge needles or other any suitably calibrated delivery device. Injection into the eye may be through the pars plana via the self-sealing needle.

In one embodiment, the ophthalmic composition is intraocularly injected (eg, into the vitreous) to treat or prevent an ophthalmic condition. When administering the ophthalmic composition by intravitreal injection, the active agents should be concentrated to minimise the volume for injection. Preferably, the volume for injection is less than about 5 ml. Volumes such as this may require compensatory drainage of the vitreous fluid to prevent increases in intraocular pressure and leakage of the injected fluid through the opening formed by the delivery needle. More preferably, the volume injected is between about 1.0 ml and 0.05 ml. Most preferably, the volume for injection is approximately 0.1 ml.

For injection, a concentration less than about 20 mg/ml may be injected, and any amount may be effective depending upon the factors previously described. Preferably a dose of less than 7 mg/ml is administered, with doses of less than 6 mg/ml, 5 mg/ml, 4 mg/ml 3 mg/ml, 2 mg/ml and 1 mg/ml being more preferred. Sample concentrations include, but are not limited to, about 5 µg/ml to about 50 µg/ml; about 25 µg/ml to about 100 µg/ml; about 100 µg/ml to about 200 µg/ml; about 200 µg/ml to about 500 µg/ml; about 500 µg/ml to about 750 µg/ml; about 500 µg/ml up to 1 mg/ml etc.

Intravitreal injection may be achieved by a variety of methods well known in the art. For example, the eye may be washed with a sterilising agent such as Betadine® and the compound of the Invention is injected in an appropriate carrier with a fine gauge needle (e.g. 27 gauge) at a position in the eye such that the compound will settle to the posterior pole towards the ventral surface. It may be necessary to prepare the eye for injection by application of positive pressure prior to injection. In some cases, paracentesis may be necessary. Local anaesthetic or general anaesthetic may be necessary.

The syringe used in practicing the method of this invention is suitably one which can accommodate a 21 to 30 gauge needle (eg a 23, 24, 25, 26 or 27 gauge needle) and is preferably of a small volume, for example 1.5 ml, or more preferably 0.5 ml. Although it is possible that the needle and syringe may be of the type where the needle is removable from the syringe, it is preferred that the arrangement is of a unitary syringe/needle construction. This would clearly limit the possibility of disengagement of the needle from the syringe. It is also preferred that the arrangement be tamper evident. The formulations of the present invention may therefore be provided in the form of a single unit dose in a pre-prepared syringe, ready for administration.

A suitable style of syringe is, for example, sold under the name of Uniject® manufactured by Becton Dickinson and Company. In this style of syringe, the material is expelled through the needle into the eye by pressure applied to the sides of a pliable reservoir supplying the needle, rather than by a plunger. As the name implies, the construction of the reservoir and needle forms a single unit.

Topical application of ophthalmic composition of the invention for the treatment or prevention of ophthalmic disorders may be as ointment, gel or eye drops. Preferably a penetrating composition comprising the peptide(s) is used. The topical ophthalmic composition may further be an in situ gellable aqueous formulation. Such a formulation comprises a gelling agent in a concentration effective to promote gelling upon contact with the eye or with lacrimal fluid in the exterior of the eye. Suitable gelling agents include, but are not limited to, thermosetting polymers such as tetra-substituted ethylene diamine block copolymers of ethylene oxide and propylene oxide (e.g., poloxamine); polycarbophil; and polysaccharides such as gellan, carrageenan (e.g., kappa-carrageenan and iota-carrageenan), chitosan and alginate gums.

The phrase "in situ gellable" as used herein embraces not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

To prepare a topical ophthalmic composition for the treatment of ophthalmic disorders, a therapeutically effective amount of the ophthalmic composition of the invention is placed in an opthalmological vehicle as is known in the art. For example, topical ophthalmic formulations containing steroids are disclosed in U.S. Pat. No. 5,041,434, whilst sustained release ophthalmic formulations of an ophthalmic drug and a high molecular weight polymer to form a highly viscous gel have been described in U.S. Pat. No. 4,271,143 and U.S. Pat. No. 4,407,792. Further GB 2007091 describes an ophthalmic composition in the form of a gel comprising an aqueous solution of a carboxyvinyl polymer, a water-soluble basic substance and an ophthalmic drug. Alternatively, U.S. Pat. No. 4,615,697, discloses a controlled release composition and method of use based on a bioadhesive and a treating agent, such as an anti-inflammatory agent.

The amount of the peptide(s) to be administered and the concentration of the compound in the topical ophthalmic composition used in the method depend upon the diluent, delivery system or selected device, the clinical condition of the patient, the side effects and the stability of the compound in the formulation. Thus, the physician employs the appropriate preparation containing the appropriate concentration of the peptide(s) and selects the amount of formulation administered, depending upon clinical experience with the patient in question or with similar patients.

Where the formulation contains two or more active agents (eg two or more peptides, or a peptide and another agent such as a tetracycline derivative etc), the active agents may be administered as a mixture, as an admixture, in the same ophthalmic composition, in separate formulations, in extended release formulations, liposomes, microcapsules, or any of the previously described embodiments. The ophthalmic composition may be administered topically, or may be injected into the eye, or one active agent may be administered topically and the other agent(s) may be injected.

The ophthalmic composition may be also administered as a slow release formulation, with a carrier formulation such as microspheres, microcapsules, liposomes, etc., as a topical ointment or solution, an intravenous solution or suspension, or in an intraocular injection, as known to one skilled in the art to treat or prevent ophthalmic disorders.

A time-release drug delivery system may be administered intraocularly to result in sustained release of the agent over a period of time. The ophthalmic composition may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and other polymers such as those disclosed in U.S. Pat. Nos. 6,667,371; 6,613,355; 6,596,296; 6,413,536; 5,968,543; 4,079, 038; 4,093,709; 4,131,648; 4,138,344; 4,180,646; 4,304,767; 4,946,931, each of which is expressly incorporated by reference herein in its entirety, or lipids that may be formulated as microspheres or liposomes. A microscopic or macroscopic ophthalmic composition may be administered through a needle, or may be implanted by suturing within the eye, for example, within the lens capsule. Delayed or extended release properties may be provided through various formulations of the vehicle (coated or uncoated microsphere, coated or uncoated capsule, lipid or polymer components, unilamellar or multilamellar structure, and combinations of the above, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety. For example, a sustained release intraocular implant may be inserted through the pars plana for implantation in the vitreous cavity.

The invention also provides a method for the treatment or prophylaxis of ophthalmic disorders with exudative/inflammatory conditions (e.g. exudative retinopathies), and/or ophthalmic disorders related to impaired retinal vessel permeability and/or integrity, said method comprising the step of administering an ophthalmic composition comprising a therapeutically effective amount of at least one peptide of the Invention in a biocompatible, biodegradable matrix, for example in the form of a gel or polymer which is preferably suited for insertion into the retina or into a cavity of the eye, anterior or posterior, as an implant. In the case that the composition is delivered as an implant, it may be incorporated in any known biocompatible biodegradable matrix as a liquid, or in the form, for example, of a micelle using known chemistry or as microparticles.

Slow or extended-release delivery systems include any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound.

In any slow release device prepared, the said peptide(s) is preferably present in an amount of about 10% to 90% by weight of the implant. More preferably, the peptide(s) is from about 50% to about 80% by weight of the implant. In a preferred embodiment, the peptide(s) comprises about 50% by weight of the implant. In a particularly preferred embodiment, the peptide(s) comprises about 70% by weight of the implant.

In one form, implants used in the method of the present invention are formulated with peptide(s) entrapped within the bio-erodible polymer matrix. Release of the agent is achieved by erosion of the polymer followed by exposure of previously entrapped agent particles to the vitreous, and subsequent dissolution and release of agent. The release kinetics achieved by this form of drug release are different than that achieved through formulations which release drug through polymer swelling, such as with hydrogels such as methylcellulose. In that case, the drug is not released through polymer erosion, but through polymer swelling, which releases drug as liquid diffuses through the pathways exposed. The parameters which determine the release kinetics include the size of the drug particles, the water solubility of the drug, the ratio of drug to polymer, the method of manufacture, the surface area exposed, and the erosion rate of the polymer.

Exemplary biocompatible, non-biodegradable polymers of particular interest include polycarbamates or polyureas, particularly polyurethanes, polymers which may be cross-linked to produce non-biodegradable polymers such as cross-linked poly(vinyl acetate) and the like. Also of particular interest are ethylene-vinyl ester copolymers having an ester content of 4% to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentanoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

Additional exemplary naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly(trifluorochloroethylene), chlorinated poly(ethylene), poly(4,4'-isopropylidene diphenylene carbonate), vinylidene chloride-acrylonitrile copolymer, vinyl chloridediethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(haloolefins), poly(vinyls), poly(acrylate), poly(methacrylate), poly(oxides), poly(esters), poly(amides), and poly(carbonates).

Diffusion of the peptide(s) from the implant may also be controlled by the structure of the implant. For example, diffusion of the peptide(s) from the implant may be controlled by means of a membrane affixed to the polymer layer comprising the drug. The membrane layer will be positioned intermediate to the polymer layer comprising the peptide(s) and the desired site of therapy. The membrane may be composed of any of the biocompatible materials indicated above, the presence of agents in addition to the peptide(s) present in the polymer, the composition of the polymer comprising the peptide(s), the desired rate of diffusion and the like. For example, the polymer layer will usually comprise a very large amount of peptide(s) and will typically be saturated. Such peptide(s)—saturated polymers may generally release the peptide(s) at a very high rate. In this situation, the release of the peptide(s) may be slowed by selecting a membrane which is of a lower peptide(s) permeability than the polymer. Due to the lower peptide(s) permeability of the membrane, the peptide(s) will remain concentrated in the polymer and the overall rate of diffusion will be determined by the peptide(s) permeability of the membrane. Therefore, the rate of release of the peptide(s) from the implant is reduced, providing for a more controlled and extended delivery of the peptide(s) to the site of therapy.

The skilled reader will appreciate that the duration over which any of the ophthalmic compositions used in the method of the invention will dwell in the ocular environment will depend, inter alia, on such factors as the physicochemical and/or pharmacological properties of the compounds employed in the formulation, the concentration of the compound employed, the bioavailability of the compound, the disease to be treated, the mode of administration and the preferred longevity of the treatment. Where that balance is struck will often depend on the longevity of the effect required in the eye and the ailment being treated.

The frequency of treatment according to the method of the invention is determined according to the disease being treated, the deliverable concentration of the peptide(s) and the method of delivery. If delivering the peptide(s) by intravitreal injection, the dosage frequency may be monthly. Preferably, the dosage frequency is every three months. The frequency of dosage may also be determined by observation, with the dosage being delivered when the previously delivered peptide(s) is visibly cleared. Once a therapeutic result is achieved, the peptide(s) can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

Ophthalmic compositions prepared for used in the method of the present invention to prevent or treat ophthalmic disorders will preferably have dwell times from hours to many months and possibly years, although the latter time period requires special delivery systems to attain such a duration. Illustrative forms of such delivery systems are disclosed elsewhere in this specification (eg below). Most preferably the formulations for use in the method of the invention will have a dwell time (ie duration in the eye) of hours (i.e. 1 to 24 hours), days (i.e. 1, 2, 3, 4, 5, 6 or 7 days) or weeks (i.e. 1, 2, 3, 4 weeks). Alternatively, the formulation will have a dwell time of at least a few months such as, 1 month, 2 months, 3 months, with dwell times of greater than 4, 5, 6, 7 to 12 months being achievable.

The methods of treatment or prophylaxis of ophthalmic conditions of the present invention may be performed alone, or in combination with one or more other therapies such as photodynamic therapy, laser surgery, laser photocoagulation or one or more biological or pharmaceutical treatments.

Laser treatment takes a number of forms, depending on the nature of the ophthalmic disorder. Disorders such as myopia may be treated with laser surgery to reshape the cornea (eg. LASIK® surgery), whilst a widely used treatment for disorders such as AMD is laser therapy which is directed to removal or blockage of blood vessels via photodynamic therapy or laser photocoagulation. Laser therapy may further be used to treat or remove neoplasm such as retinoblastomas or pseudogliomas.

Photocoagulation involves the use of a laser to seal leaking blood vessels, slow the growth of abnormal blood vessels and/or destroy new blood vessels within the eye. In addition, the laser can be used to seal the retina to the eye, helping to prevent retinal detachment. For example, focal laser treatment may be applied to microaneurysms identified in diabetic retinopathy.

Photodynamic therapy involves the use of a photoactive drug (eg Visudyne®) and a laser to destroy abnormal blood vessels. Visudyne® is injected into the blood and activated with a laser, effectively destroying the blood vessels. This treatment may require several sessions to be effective. A wide range of theories have been proposed to explain the beneficial effects of retinal laser photocoagulation in delaying retinal angiogenesis, however, the underlying molecular mechanism remains to be elucidated.

The therapeutic effects of laser photocoagulation are thought to be due to the destruction of photoreceptors, the highest oxygen consumers in the retina. Subsequently, these photoreceptors are replaced by glial cells allowing increased oxygen diffusion from the choroid to the inner retina thereby relieving inner retinal hypoxia. This improved oxygenation triggers a two-pronged cascade of events where: (1) constriction of the retinal arteries results in decreased hydrostatic pressure in capillaries and the constriction of capillaries and venules; and (2) the cellular production of VEGF is inhibited. Together, these effects are believed to ultimately result in the inhibition of neovascularization and a decrease in oedema. Cell proliferation and regulation of cellular proteins are induced by the laser photocoagulation, and their therapeutic effect might be an essential part of the physiological response.

However, a complication of laser treatment (either photo-dynamic laser therapy or laser photocoagulation) is inflammation, leading to further oedema. This may also occur after laser therapy to remove or treat ocular neoplasm. In addition, laser treatment is not always a permanent cure as the blood vessels may begin to grow again, and microaneurysms may reform. Furthermore, laser treatment of abnormal blood vessels cannot be performed on vessels located in certain regions of the retina, such as the central region of the macula.

Therefore, in an embodiment of the invention, where laser treatment of the retina is indicted, administration of an ophthalmic composition of the Invention may be carried out by injection before or after the laser treatment. Administration of the peptide(s) of the Invention may reduce, eliminate or prevent oedema before or after laser therapy and may therefore reduce or eliminate one of the side effects of laser therapy.

In another embodiment, the Invention resides in a method for reducing ocular irritation comprising the step of administering to a patient an ophthalmic composition of the Invention to a patient following corneal surgery (e.g., LASIK® surgery, photorefractive keratectomy (PRK), or other corneal procedures). Such treatment reduces or inhibits the exudation of fluids in the eye which may cloud the cornea or the vitreous.

In addition to the other compounds previously described, ophthalmic composition of the invention may further comprise anti-angiogenic agents designed to block the actions of VEGF on endothelial cells in combined therapies. Examples of agents that can be employed in the method of the invention are: (a) Lucentis® developed by Genentech; and (b) Macugen® developed by Eyetech Pharmaceuticals. Lucentis® and Macugen® are compounds that are injected into the vitreous and are potent anti-angiogenic compounds.

In another aspect of the invention, the ophthalmic composition of the invention may further comprise a compound selected in the group consisting of a glucocorticoid (e.g. prednisolone, prednisone), an oestrogen (e.g. oestrodiol), an androgen (e.g. testosterone) retinoic acid derivatives (e.g. 9-cis-retinoic acid, 13-trans-retinoic acid, all-trans retinoic acid), a vitamin D derivative (e.g. calcipotriol, calcipotriene), a non-steroidal anti-inflammatory agent, a vitamin D derivative, an anti-infective agent, a protein kinase C inhibitor, a MAP kinase inhibitor, an anti-apoptotic agent, a growth factor, a nutrient vitamin, an unsaturated fatty acid, and/or ocular anti-infective agents, for the treatment of the ophthalmic disorders set forth herein. In still other embodiments of the invention, a mixture of these agents may be used. Ocular anti-infective agents that may be used include, but are not limited to, penicillins (ampicillin, aziocillin, carbenicillin, dicloxacillin, methicillin, nafcillin, oxacillin, penicillin G, piperacillin, and ticarcillin), cephalosporins (cefamandole, cefazolin, cefotaxime, cefsulodin, ceftazidime, ceftriaxone, cephalothin, and moxalactam), aminoglycosides (amikacin, gentamicin, netilmicin, tobramycin, and neomycin), miscellaneous agents such as aztreonam, bacitracin, ciprofloxacin, clindamycin, chloramphenicol, cotrimoxazole, fusidic acid, imipenem, metronidazole, teicoplanin, and vancomycin), antifungals (amphotericin B, clotrimazole, econazole, fluconazole, flucytosine, itraconazole, ketoconazole, miconazole, natamycin, oxiconazole, and terconazole), antivirals (acyclovir, ethyldeoxyuridine, foscarnet, ganciclovir, idoxuridine, trifluridine, vidarabine, and (S)-1-(3-dydroxy-2-phospho-nyluethoxypropyl) cytosine (HPMPC)), antineoplastic agents (cell cycle (phase) nonspecific agents such as alkylating agents (chlorambucil, cyclophosphamide, mechlorethamine, melphalan, and busulfan), anthracycline antibiotics (doxorubicin, daunomycin, and dactinomycin), cisplatin, and nitrosoureas), antimetabolites such as antipyrimidines (cytarabine, fluorouracil and azacytidine), antifolates (methotrexate), antipurines (mercaptopurine and thioguanine), bleomycin, vinca alkaloids (vincrisine and vinblastine), podophylotoxins (etoposide (VP-16)), and nitrosoureas (carmustine, (BCNU)), immunosuppressant agents such as cyclosporin A and SK506, and anti-inflammatory or suppressive agents (inhibitors), and inhibitors of proteolytic enzymes such as plasminogen activator inhibitors. Doses for topical and sub-conjunctival administration of the above agents, as well as intravitreal dose and vitreous half-life may be found in Intravitreal Surgery Principles and Practice, Peyman G A and Shulman, J. Eds., 2nd edition, 1994, Appleton-Longe, the relevant sections of which are expressly incorporated by reference herein.

According to another embodiment, the invention provides methods of using serine protease inhibitors in a method for treating and/or preventing ophthalmic disorders and compositions for such use. According to another embodiment, the invention provides methods of using kallikrein inhibitors in a method for treating and/or preventing ophthalmic disorders and compositions for such use. Examples of said inhibitors are peptides such as those disclosed above, or inhibitors selected among direct and indirect inhibitors. The term "direct inhibitor" as used herein, refers to an agent able to interfere with the production of bradykinin and/or kallidin. It relates to an agent able to decrease (e.g. by at least 10%, 20%, or 30% or more) the activity of kallikrein either in vitro or in vivo after administration to a mammal, such as a human. According to a more preferred embodiment, said direct inhibitor is an agent which decreases (e.g. by at least 10%, 20%, or 30%, preferably 50%, more preferably 75% or 85%, and most preferably 95%) the kininogenase activity of kallikrein. These functional characterisations of the direct inhibitor can be tested using well known assay methods, such as for example those disclosed in Gallimore et al, 1979, Thromb Res 16, 695-703; Kondo et al., 1984, Endocrinol Jpn., 31, 635-643. "Partial inhibitor" refers to a compound which acts as the inhibitor but that produces a weak maximum inhibitory response. This term is well known in the art. Exemplary kallikrein inhibitors (e.g. plasma kallikrein inhibitors) include those described in U.S. Pat. No. 6,333,402, U.S. Pat. No. 6,057,287, U.S. Pat. No. 6,010,880 or Zhang et al., 2006, Med. Chem., 2, 545-553 the contents of which are incorporated herein by reference in their entirety.

The term "indirect inhibitor" as used herein, refers for example to an agent able to interfere specifically with the kallikrein gene expression, and more particularly with the kallikrein mRNA. According to one embodiment of the present invention, the said inhibitor or partial inhibitor is selected in the group consisting of antisense RNA, siRNA, ribozyme, miRNA, shRNA, i.e. compounds that reduce the expression levels of said kallikrein, preferably plasma kallikrein. According to another embodiment, the term "indirect inhibitor" as used herein, refers to an anti-kallikrein or anti-prekallikrein antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F (ab') 2 fragments which can be generated by treating the antibody with an enzyme such as papain or pepsin, respectively. The antibody can be a polyclonal, monoclonal, recombinant, e.g. a chimeric or humanized, fully human, non-human, e.g. murine or single chain antibody. The antibody can be coupled to a toxin or imaging agent. Additionally, chimeric, humanized, and completely human antibodies are also within the scope of the invention. Chimeric, humanized, but most preferably, completely human antibodies are desirable for applications which include repeated administration, e.g., therapeutic treatment of human patients. These terms and methods for producing these antibodies by recombinant DNA techniques are widely known in the art (see for example EP184187, EP171496, EP173494, WO 86/01533, U.S. Pat. No. 4,816,567).

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

The present invention is not to be limited in scope by the specific embodiments described herein, which are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

EXAMPLES

Figures

FIG. 1—Effect of intra-vitreous SEQ ID NO: 23 on OCT-measured maximal retinal thickness in a pig model of RVO. Maximal retina thickness was determined 24 h after RVO from Optical Coherence Tomography images. Values are mean±s.e.mean. Comparison of values was performed by a one-way ANOVA following by a student t-test.

Figure 2:
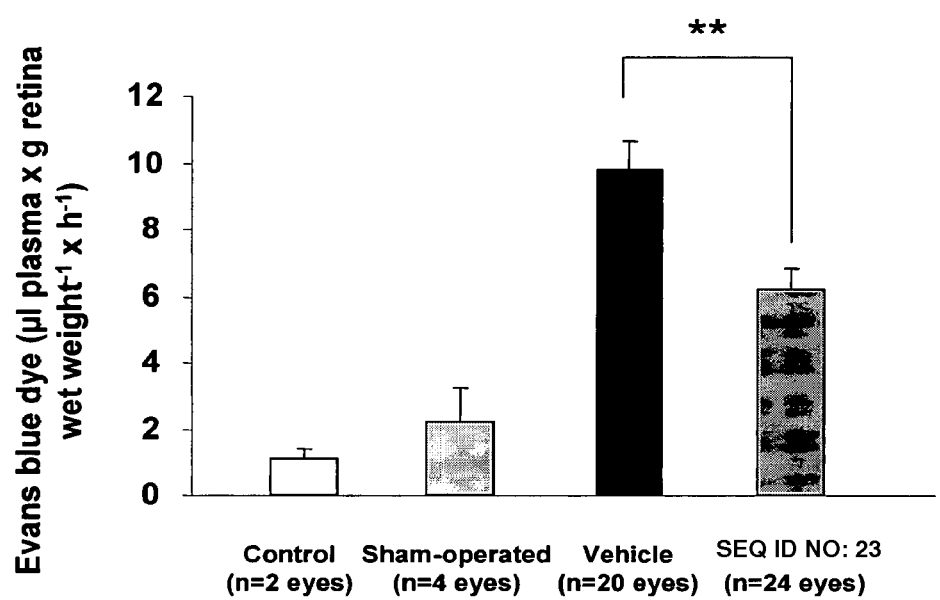

FIG. 2—Effect of intra-vitreous SEQ ID NO: 23 on the development of extra-cellular retinal oedema in a pig model of RVO.

The amount of Evans Blue dye concentration into the retinal tissue reflects plasma extravasation and the extent of oedema. Control values represent retina Evans Blue Dye content of 2 eyes that were left non-operated and non-treated whilst sham-operated eyes (n=4) were submitted to the surgical procedure but without occlusion (See Methods). Values are mean±s.e.mean. Comparison of values was performed by a one-way ANOVA following by a student t-test. **, $p<0.01$

Example 1

Materials and Methods

Pig Preparation

Mixed breed (Large White×Landrace×Pietrain) female pigs weighing 50 to 60 kg aged of 5 to 6 months were used. Following intramuscular injection of ketamine (10 mg/kg), azaperone (2 mg/kg) and atropine (0.02 mg/kg), anesthesia was induced by intravenous sodium thiopental (10 mg/kg). After tracheal intubation, anesthesia was maintained with isoflurane (1-2% in 100% $O_2$) using a Hallowell ventilator (15 to 20 rpm; pressure at 20 $cmH_2O$).

Three-lead ECG (lead II configuration), body temperature, arterial blood pressure and blood gases were continuously monitored.

Procedure of Retinal Vein Occlusion (RVO)

Pupil was dilated by tropicamide. Conjunctival disinsertion was followed by a 0.9 mm sclerotomy, 3 mm from the limbus. The fundus was observed using a plano-concave lens and the axial light of the operating microscope (Microscope OPMI 6-C, Zeiss, Germany). Branch retinal vein occlusion (RVO) of the major temporal vein was performed by transvitreal cauterization using a 300 micron probe (GN 300, Aesculap, Tuttlingen, Germany). Completion of the occlusion was assessed by the complete arrest of blood flow upstream of the occlusion site. Both eyes were submitted to RVO.

Sham-operation was performed in two pigs (4 eyes) as follows pupil was dilated by tropicamide. Conjunctival disinsertion was followed by a 0.9 mm sclerotomy, 3 mm from the limbus. The fundus was observed using a plano-concave lens and the axial light of the operating microscope (Microscope OPMI 6-C, Zeiss, Germany).

One pig was non-operated and non-treated.

Drug Treatments

The Number of Animals Tested has been Increased.

Animals that were submitted to RVO were randomised to receive either the vehicle or the drug (10 to 14 pigs/group). Accordingly, 100 µl of SEQ ID No 23 in solution (dosage of 21.2 µg/eye) or of the corresponding vehicle (saline) was injected intra-vitreally, immediately following RVO.

SEQ ID No 23 (also named DX 88 in Figures) is a peptide of the following sequence:

```
Glu Ala Met His Ser Phe Cys Ala Phe Lys Ala Asp Asp Gly Pro Cys

Arg Ala Ala His Pro Arg Trp Phe Phe Asn Ile Phe Thr Arg Gln Cys Glu

Glu Phe Ile Tyr Gly Gly Cys Glu Gly Asn Gln Asn Arg Phe Glu Ser Leu

Glu Glu Cys Lys Lys Met Cys Thr Arg Asp
```

Measurement of Retinal Maximal Thickness and Oedema

Twenty four hours later, the animals will be anesthetized again, and a 40 MHz ultrasonographic examination of the posterior retina will be performed. The scan will be oriented so as to encompass the normal and edematous retina. This will ensure an optimal placement of the OCT scan. Optical coherence tomography (Stratus OCT, Zeiss Humphrey, Dublin, Calif.) will document the maximal thickening of the central retina and/or the presence of subretinal fluid.

After OCT measurement, each animal received Evans Blue dye at 45 mg/kg i.v. and venous blood samples (approximately 1 ml) were obtained at 15 minutes intervals for 2 hours. These blood samples were centrifuged at 12,000 rpm for 15 min. After the dye had circulated for 2 hours, the animals were infused for 10 minutes via the left cardiac ventricle with citrate buffer (0.05 M, pH 3.5) and blood was collected from the right cardiac ventricle. The whole infusion volume was 5l over 10 minutes. After infusion, both eyes were enucleated and bisected at equator. The retinas were carefully dissected out. Retina were prepared, weighed and desiccated in Speed-Vac for 5 hours. Evans Blue dye was extracted by incubating each retina in 500 µl formamide for 18 hours at 70° C. The supernatant was filtered through Ultrafree-MC at 3,000 rpm for 2 hours. Evans Blue dye concentration in plasma samples and in retina tissue was measured by spectrophotometry at both 620 nm and 740 nm.

Thus, in an embodiment of the present invention, a model of RVO in the pig is described which allows evaluation of drugs on retinal thickness and oedema. An example is given with the evaluation of SEQ ID No 23 in this model.

Example 2

Effect of Seq.Id.No 23 in a Pig Model of Acute Macular Oedema Induced by RVO

At 24 h, spontaneous reperfusion of retinal vein was observed in 10% and 30% of vehicle- and SEQ ID No 23-treated eyes, respectively (See Table 1 below).

Evans Blue dye retinal concentration, which represents the extent of extra-cellular oedema, was markedly increased 24 h following RVO (FIG. 2). This was significantly ($p<0.01$) reduced by 47% in SEQ. ID. No 23-treated pigs (FIG. 1).

After repeated experiments, we concluded that in the animal model selected, the peptide SEQ ID No 23 did not modify the increase of maximal retinal thickness as measured by OCT (FIG. 1). We concluded that the method of measurement used was actually not adapted to the present animal model. Our interpretation is that SEQ. ID. No 23 specifically targets vascular leakage which appears to be minor in respect to the ischemic oedema component in the pig RVO model. In addition, OCT images revealed that the retina presents an irregular thickening and bumpy surface after RVO occlusion that makes OCT-based measurements poorly reliable.

TABLE 1

Effect of SEQ. ID. N° 23 on the rate of spontaneous retinal vein reperfusion 24 h after RVO in the pig

| | Number of pigs/eyes submitted to RVO | Number (%) of reperfused retinal vein at 24 h |
|---|---|---|
| Vehicle | 10/20 | 2 (10%) |
| SEQ. ID. N° 23 | 13/26 | 8 (30%) |

The invention claimed is:

1. A method for treating an ophthalmic disorder in a subject, comprising administering to said subject a therapeutically effective amount of a peptide comprising the amino acid sequence of SEQ ID NO. 23, wherein the ophthalmic disorder is macular oedema or retinal ischemia, thereby treating the ophthalmic disorder in said subject.

2. A method for treating macular oedema induced by a retinopathy in a subject, comprising intreavitrally administering to said subject a therapeutically effective amount of a peptide comprising the amino acid sequence of SEQ ID NO. 23, thereby treating macular oedema induced by a retinopathy in said subject.

3. The method of claim 2, wherein said retinopathy is a retinal venous occlusion.

* * * * *

SEQUENCE LISTING

```
<160> NUMBER OF SEQ ID NOS: 44

<210> SEQ ID NO 1
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Variable amino acid
<220> FEATURE:
<221> NAME/KEY: MOD_RES
<222> LOCATION: (6)..(11)
<223> OTHER INFORMATION: Variable amino acid
<220> FEATURE:
<221> NAME/KEY: MOD_RES
<222> LOCATION: (13)
```

<223> OTHER INFORMATION: Variable amino acid
<220> FEATURE:
<221> NAME/KEY: MOD_RES
<222> LOCATION: (15)..(29)
<223> OTHER INFORMATION: Variable amino acid
<220> FEATURE:
<221> NAME/KEY: MOD_RES
<222> LOCATION: (31)..(32)
<223> OTHER INFORMATION: Variable amino acid
<220> FEATURE:
<221> NAME/KEY: MOD_RES
<222> LOCATION: (34)..(35)
<223> OTHER INFORMATION: Variable amino acid
<220> FEATURE:
<221> NAME/KEY: MOD_RES
<222> LOCATION: (39)..(50)
<223> OTHER INFORMATION: Variable amino acid
<220> FEATURE:
<221> NAME/KEY: MOD_RES
<222> LOCATION: (52)..(54)
<223> OTHER INFORMATION: Variable amino acid
<220> FEATURE:
<221> NAME/KEY: MOD_RES
<222> LOCATION: (56)..(58)
<223> OTHER INFORMATION: Variable amino acid
<220> FEATURE:
<223> OTHER INFORMATION: see specification as filed for detailed
      description of substitutions and preferred embodiments

<400> SEQUENCE: 1

Xaa Xaa Xaa Xaa Cys Xaa Xaa Xaa Xaa Xaa Xaa Gly Xaa Cys Xaa Xaa
 1               5                  10                  15

Xaa Xaa Xaa Xaa Xaa Xaa Xaa Xaa Xaa Xaa Xaa Xaa Xaa Cys Xaa Xaa
                20                  25                  30

Phe Xaa Xaa Gly Gly Cys Xaa Xaa Xaa Xaa Xaa Xaa Xaa Xaa Xaa Xaa
            35                  40                  45

Xaa Xaa Cys Xaa Xaa Xaa Cys Xaa Xaa Xaa
        50                  55

<210> SEQ ID NO 2
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His Ser Phe Cys Ala Phe Lys Ala Asp Asp Gly Pro Cys Arg Ala
 1               5                  10                  15

Ala His Pro Arg Trp Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

<210> SEQ ID NO 3
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(11)
<223> OTHER INFORMATION: Variable amino acid
<220> FEATURE:

```
<221> NAME/KEY: MOD_RES
<222> LOCATION: (13)
<223> OTHER INFORMATION: Variable amino acid
<220> FEATURE:
<221> NAME/KEY: MOD_RES
<222> LOCATION: (15)..(19)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (31)..(32)
<223> OTHER INFORMATION: Variable amino acid
<220> FEATURE:
<221> NAME/KEY: MOD_RES
<222> LOCATION: (34)..(35)
<223> OTHER INFORMATION: Variable amino acid
<220> FEATURE:
<221> NAME/KEY: MOD_RES
<222> LOCATION: (39)
<223> OTHER INFORMATION: Variable amino acid
<220> FEATURE:
<223> OTHER INFORMATION: see specification as filed for detailed
      description of substitutions and preferred embodiments

<400> SEQUENCE: 3

Met His Ser Phe Cys Ala Phe Lys Ala Xaa Xaa Gly Xaa Cys Xaa Xaa
1               5                   10                  15

Xaa Xaa Xaa Arg Xaa Phe Phe Asn Ile Phe Thr Arg Gln Cys Xaa Xaa
            20                  25                  30

Phe Xaa Xaa Gly Gly Cys Xaa Gly Asn Gln Asn Arg Phe Glu Ser Leu
        35                  40                  45

Glu Glu Cys Lys Lys Met Cys Thr Arg Asp
    50                  55

<210> SEQ ID NO 4
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met His Ser Phe Cys Ala Phe Lys Ala Asp Asp Gly Pro Cys Lys Ala
1               5                   10                  15

Asn His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
```

```
                    20                  25                  30

Phe Thr Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
            35                  40                  45

Glu Glu Cys Lys Lys Met Cys Thr Arg Asp
    50                  55

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met His Ser Phe Cys Ala Phe Lys Ala Asp Asp Gly His Cys Lys Ala
1               5                   10                  15

Ser Leu Pro Arg Phe Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 8
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met His Ser Phe Cys Ala Phe Lys Ala Asp Asp Gly His Cys Lys Ala
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 9
```

```
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met His Ser Phe Cys Ala Phe Lys Ala Asp Asp Gly His Cys Lys Gly
1               5                   10                  15

Ala His Leu Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 10
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met His Ser Phe Cys Ala Phe Lys Ala Asp Asp Gly Arg Cys Lys Gly
1               5                   10                  15

Ala His Leu Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 11
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met His Ser Phe Cys Ala Phe Lys Ala Asp Gly Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met His Ser Phe Cys Ala Phe Lys Ala Asp Asp Gly Pro Cys Arg Ala
```

```
            1               5                  10                  15
Ala His Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55
```

<210> SEQ ID NO 13
<211> LENGTH: 58
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Met His Ser Phe Cys Ala Phe Lys Ala Asp Val Gly Arg Cys Arg Gly
1               5                   10                  15

Ala His Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55
```

<210> SEQ ID NO 14
<211> LENGTH: 58
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

```
Met His Ser Phe Cys Ala Phe Lys Ala Asp Val Gly Arg Cys Arg Gly
1               5                   10                  15

Ala Gln Pro Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55
```

<210> SEQ ID NO 15
<211> LENGTH: 58
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

```
Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55
```

```
<210> SEQ ID NO 16
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met His Ser Phe Cys Ala Phe Lys Ala Glu Gly Gly Ser Cys Arg Ala
 1               5                  10                  15

Ala His Gln Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55

<210> SEQ ID NO 17
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met His Ser Phe Cys Ala Phe Lys Ala Asp Asp Gly Pro Cys Arg Gly
 1               5                  10                  15

Ala His Leu Arg Phe Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55

<210> SEQ ID NO 18
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met His Ser Phe Cys Ala Phe Lys Ala Asp Asp Gly His Cys Arg Gly
 1               5                  10                  15

Ala Leu Pro Arg Trp Phe Phe Asn Ile Phe Thr Arg Gln Cys Glu Glu
                20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
        50                  55

<210> SEQ ID NO 19
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 19

Met His Ser Phe Cys Ala Phe Lys Ala Asp Ser Gly Asn Cys Arg Gly
1               5                   10                  15

Asn Leu Pro Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                  55

<210> SEQ ID NO 20
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met His Ser Phe Cys Ala Phe Lys Ala Asp Ser Gly Arg Cys Arg Gly
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                  55

<210> SEQ ID NO 21
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
50                  55

<210> SEQ ID NO 22
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

```
Glu Glu Cys Lys Lys Met Cys Thr Arg Asp
    50                  55

<210> SEQ ID NO 23
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
                20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
    50                  55                  60

<210> SEQ ID NO 24
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (17)..(21)
<223> OTHER INFORMATION: Variable amino acid
<220> FEATURE:
<221> NAME/KEY: MOD_RES
<222> LOCATION: (23)
<223> OTHER INFORMATION: Variable amino acid
<220> FEATURE:
<221> NAME/KEY: MOD_RES
<222> LOCATION: (33)..(34)
<223> OTHER INFORMATION: Variable amino acid
<220> FEATURE:
<221> NAME/KEY: MOD_RES
<222> LOCATION: (36)..(37)
<223> OTHER INFORMATION: Variable amino acid
<220> FEATURE:
<221> NAME/KEY: MOD_RES
<222> LOCATION: (41)
<223> OTHER INFORMATION: Variable amino acid
<220> FEATURE:
<223> OTHER INFORMATION: see specification as filed for detailed
      description of substitutions and preferred embodiments

<400> SEQUENCE: 24

Glu Ala Met His Ser Phe Cys Ala Phe Lys Ala Xaa Xaa Gly Xaa Cys
1               5                   10                  15

Xaa Xaa Xaa Xaa Xaa Arg Xaa Phe Phe Asn Ile Phe Thr Arg Gln Cys
                20                  25                  30

Xaa Xaa Phe Xaa Xaa Gly Gly Cys Xaa Gly Asn Gln Asn Arg Phe Glu
            35                  40                  45

Ser Leu Glu Glu Cys Lys Lys Met Cys Thr Arg Asp
```

<210> SEQ ID NO 25
<211> LENGTH: 60
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Glu Ala Met His Ser Phe Cys Ala Phe Lys Ala Asp Asp Gly Pro Cys
1               5                   10                  15

Lys Ala Asn His Leu Arg Phe Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 26
<211> LENGTH: 60
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Glu Ala Met His Ser Phe Cys Ala Phe Lys Ala Asp Asp Gly His Cys
1               5                   10                  15

Lys Ala Asn His Gln Arg Phe Phe Phe Asn Ile Phe Thr Arg Gln Cys
            20                  25                  30

Glu Glu Phe Thr Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 27
<211> LENGTH: 60
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Glu Ala Met His Ser Phe Cys Ala Phe Lys Ala Asp Asp Gly His Cys
1               5                   10                  15

Lys Ala Asn His Gln Arg Phe Phe Phe Asn Ile Phe Thr Arg Gln Cys
            20                  25                  30

Glu Gln Phe Thr Tyr Gly Gly Cys Ala Gly Asn Gln Asn Arg Phe Glu
        35                  40                  45

Ser Leu Glu Glu Cys Lys Lys Met Cys Thr Arg Asp
    50                  55                  60

<210> SEQ ID NO 28
<211> LENGTH: 60
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Glu Ala Met His Ser Phe Cys Ala Phe Lys Ala Asp Asp Gly His Cys
1               5                   10                  15

Lys Ala Ser Leu Pro Arg Phe Phe Asn Ile Phe Thr Arg Gln Cys
            20                  25                  30

Glu Glu Phe Ile Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 29
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ala Met His Ser Phe Cys Ala Phe Lys Ala Asp Asp Gly His Cys
1               5                   10                  15

Lys Ala Asn His Gln Arg Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 30
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Ala Met His Ser Phe Cys Ala Phe Lys Ala Asp Asp Gly His Cys
1               5                   10                  15

Lys Gly Ala His Leu Arg Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45

Ser Leu Glu Glu Cys Lys Lys Met Cys Thr Arg Asp
    50                  55                  60

<210> SEQ ID NO 31
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ala Met His Ser Phe Cys Ala Phe Lys Ala Asp Asp Gly Arg Cys
1               5                   10                  15

Lys Gly Ala His Leu Arg Phe Phe Asn Ile Phe Thr Arg Gln Cys
            20                  25                  30

Glu Glu Phe Ile Tyr Gly Gly Cys Glu Gly Asn Gln Asn Arg Phe Glu

```
                35                  40                  45
Ser Leu Glu Glu Cys Lys Lys Met Cys Thr Arg Asp
     50                  55                  60

<210> SEQ ID NO 32
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Glu Ala Met His Ser Phe Cys Ala Phe Lys Ala Asp Gly Gly Arg Cys
 1               5                  10                  15

Arg Gly Ala His Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
     50                  55                  60

<210> SEQ ID NO 33
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
     50                  55                  60

<210> SEQ ID NO 34
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ala Met His Ser Phe Cys Ala Phe Lys Ala Asp Val Gly Arg Cys
 1               5                  10                  15

Arg Gly Ala His Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
     50                  55                  60

<210> SEQ ID NO 35
<211> LENGTH: 60
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 35

Glu Ala Met His Ser Phe Cys Ala Phe Lys Ala Asp Val Gly Arg Cys
1               5                   10                  15

Arg Gly Ala Gln Pro Arg Phe Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 36
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Ala Met His Ser Phe Cys Ala Phe Lys Ala Asp Asp Gly Ser Cys
1               5                   10                  15

Arg Ala Ala His Leu Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 37
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Ala Met His Ser Phe Cys Ala Phe Lys Ala Glu Gly Gly Ser Cys
1               5                   10                  15

Arg Ala Ala His Gln Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 38
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Ala Met His Ser Phe Cys Ala Phe Lys Ala Asp Asp Gly Pro Cys
1               5                   10                  15

Arg Gly Ala His Leu Arg Phe Phe Phe Asn Ile Phe Thr Arg Gln Cys

```
                  20                  25                  30

Glu Glu Phe Ser Tyr Gly Gly Cys Gly Gly Asn Gln Asn Arg Phe Glu
            35                  40                  45

Ser Leu Glu Glu Cys Lys Lys Met Cys Thr Arg Asp
    50                  55                  60

<210> SEQ ID NO 39
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ala Met His Ser Phe Cys Ala Phe Lys Ala Asp Asp Gly His Cys
1               5                   10                  15

Arg Gly Ala Leu Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
            35                  40                  45

Ser Leu Glu Glu Cys Lys Lys Met Cys Thr Arg Asp
    50                  55                  60

<210> SEQ ID NO 40
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ala Met His Ser Phe Cys Ala Phe Lys Ala Asp Ser Gly Asn Cys
1               5                   10                  15

Arg Gly Asn Leu Pro Arg Phe Phe Phe Asn Ile Phe Thr Arg Gln Cys
            20                  25                  30

Glu Glu Phe Ser Tyr Gly Gly Cys Gly Gly Asn Gln Asn Arg Phe Glu
            35                  40                  45

Ser Leu Glu Glu Cys Lys Lys Met Cys Thr Arg Asp
    50                  55                  60

<210> SEQ ID NO 41
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ala Met His Ser Phe Cys Ala Phe Lys Ala Asp Ser Gly Arg Cys
1               5                   10                  15

Arg Gly Asn His Gln Arg Phe Phe Phe Asn Ile Phe Thr Arg Gln Cys
            20                  25                  30

Glu Glu Phe Ser Tyr Gly Gly Cys Gly Gly Asn Gln Asn Arg Phe Glu
            35                  40                  45

Ser Leu Glu Glu Cys Lys Lys Met Cys Thr Arg Asp
    50                  55                  60

<210> SEQ ID NO 42
```

```
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Ala Met His Ser Phe Cys Ala Phe Lys Ala Asp Gly Gly Arg Cys
1               5                   10                  15

Arg Ala Ile Gln Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Ala Met His Ser Phe Cys Ala Phe Lys Ala Asp Asp Gly Arg Cys
1               5                   10                  15

Arg Gly Ala His Pro Arg Trp Phe Phe Asn Ile Phe Thr Arg Gln Cys
            20                  25                  30

Glu Glu Phe Ser Tyr Gly Gly Cys Gly Gly Asn Gln Asn Arg Phe Glu
        35                  40                  45

Ser Leu Glu Glu Cys Lys Lys Met Cys Thr Arg Asp
    50                  55                  60

<210> SEQ ID NO 44
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Variable amino acid
<220> FEATURE:
<221> NAME/KEY: MOD_RES
<222> LOCATION: (8)..(13)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (17)..(31)
<223> OTHER INFORMATION: Variable amino acid
<220> FEATURE:
<221> NAME/KEY: MOD_RES
<222> LOCATION: (33)..(34)
<223> OTHER INFORMATION: Variable amino acid
<220> FEATURE:
<221> NAME/KEY: MOD_RES
<222> LOCATION: (36)..(37)
<223> OTHER INFORMATION: Variable amino acid
<220> FEATURE:
<221> NAME/KEY: MOD_RES
<222> LOCATION: (41)..(52)
```

```
<223> OTHER INFORMATION: Variable amino acid
<220> FEATURE:
<221> NAME/KEY: MOD_RES
<222> LOCATION: (54)..(56)
<223> OTHER INFORMATION: Variable amino acid
<220> FEATURE:
<221> NAME/KEY: MOD_RES
<222> LOCATION: (58)..(60)
<223> OTHER INFORMATION: Variable amino acid
<220> FEATURE:
<223> OTHER INFORMATION: see specification as filed for detailed
      description of substitutions and preferred embodiments

<400> SEQUENCE: 44

Glu Ala Xaa Xaa Xaa Xaa Cys Xaa Xaa Xaa Xaa Xaa Xaa Gly Xaa Cys
 1               5                  10                  15

Xaa Xaa Xaa Xaa Xaa Xaa Xaa Xaa Xaa Xaa Xaa Xaa Xaa Xaa Xaa Cys
            20                  25                  30

Xaa Xaa Phe Xaa Xaa Gly Gly Cys Xaa Xaa Xaa Xaa Xaa Xaa Xaa
        35                  40                  45

Xaa Xaa Xaa Xaa Cys Xaa Xaa Xaa Cys Xaa Xaa Xaa
 50                  55                  60
```